Figure 1:
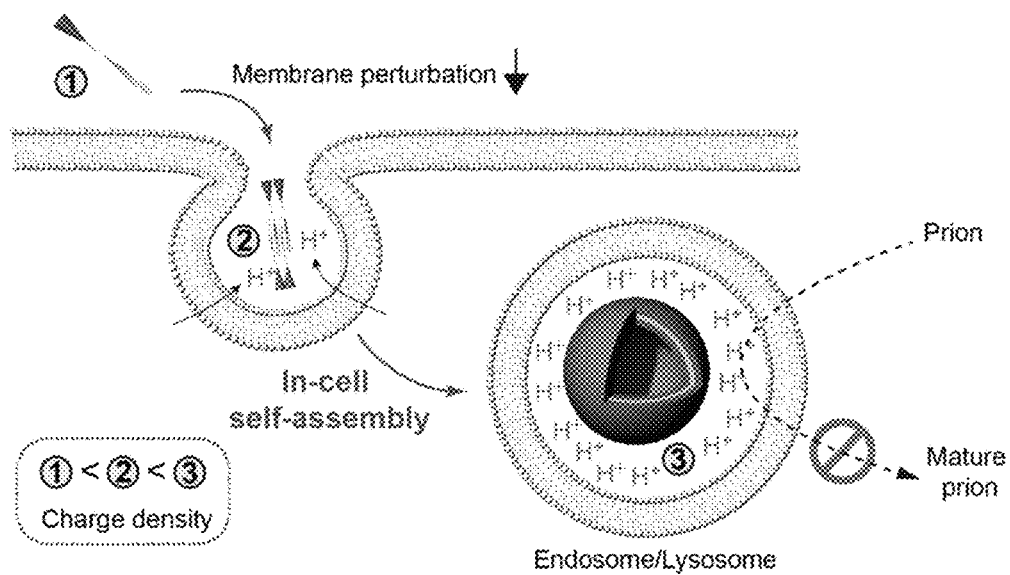

US010232012B2

(12) United States Patent
Lim et al.

(10) Patent No.: US 10,232,012 B2
(45) Date of Patent: Mar. 19, 2019

(54) INTRACELLULAR PH-RESPONSIVE FUSION PEPTIDE AND PHARMACEUTICAL COMPOSITION FOR REDUCING ABNORMAL PRION PROTEIN AGGREGATION OR MISFOLDING

(71) Applicants: INDUSTRY-ACADEMIC COOPERATION FOUNDATION, YONSEI UNIVERSITY, Seoul (KR); INDUSTRY-UNIVERSITY COOPERATION FOUNDATION HANYANG UNIVERSITY ERICA CAMPUS, Gyeonggi-do (KR)

(72) Inventors: Yong beom Lim, Seoul (KR); Chong suk Ryou, Gyeonggido (KR)

(73) Assignees: INDUSTRY-ACADEMIC COOPERATION FOUNDATION, YONSEI UNIVERSITY, Seoul (KR); INDUSTRY-UNIVERSITY COOPERATION FOUNDATION HANYANG UNIVERSITY ERICA CAMPUS, Gyeonggi-Do (KR)

( * ) Notice: Subject to any disclaimer, the term of this patent is extended or adjusted under 35 U.S.C. 154(b) by 0 days.

(21) Appl. No.: 15/827,246

(22) Filed: Nov. 30, 2017

(65) Prior Publication Data

US 2018/0147255 A1 May 31, 2018

(30) Foreign Application Priority Data

Nov. 30, 2016 (KR) ........................ 10-2016-0161767

(51) Int. Cl.

| | |
|---|---|
| *C07K 5/00* | (2006.01) |
| *C07K 4/00* | (2006.01) |
| *C07K 2/00* | (2006.01) |
| *C07K 7/00* | (2006.01) |
| *C07K 14/00* | (2006.01) |
| *A61K 38/00* | (2006.01) |
| *A61K 49/00* | (2006.01) |
| *A61B 5/00* | (2006.01) |
| *A61K 38/17* | (2006.01) |
| *C07K 14/47* | (2006.01) |
| *A61K 38/16* | (2006.01) |
| *A61K 9/127* | (2006.01) |
| *C07K 16/00* | (2006.01) |
| *C07K 19/00* | (2006.01) |

(52) U.S. Cl.
CPC ............ *A61K 38/16* (2013.01); *A61K 9/1271* (2013.01); *A61K 9/1277* (2013.01); *C07K 14/00* (2013.01); *C07K 16/00* (2013.01); *C07K 19/00* (2013.01)

(58) Field of Classification Search
CPC .......... A61K 47/42; A61K 2039/55516; A61K 38/00; C07K 2319/00; C07K 7/06; C12N 2533/50
See application file for complete search history.

(56) References Cited

U.S. PATENT DOCUMENTS

| | | | | |
|---|---|---|---|---|
| 9,757,428 B2 * | 9/2017 | Miller | A61K 39/12 | |
| 2007/0271630 A1 * | 11/2007 | Boukharov | C07K 14/4354 | 800/279 |
| 2016/0199440 A1 * | 7/2016 | Miller | A61K 39/12 | 424/210.1 |

FOREIGN PATENT DOCUMENTS

| | | |
|---|---|---|
| KR | 1020150146181 | 12/2015 |

OTHER PUBLICATIONS

Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Anger. Neurotoxicology 1991. 12: 403-13.*
't Hart et al. Curr. Opin. Neurol. 2003. 16: 375-383.*
Tayebati. Mech. Ageing Dev. 2006. 127: 100-8.*
Murphy, "Peptide Aggregation in Neurodegenerative Disease", Annu. Rev. Biomed. Eng., 2002, 4:155-74.
Mandal et al., "Self-assembly of peptides to nanostructures", Org. Biomol. Chem., 2014, 12, 3544-3561.

* cited by examiner

*Primary Examiner* — Chang-Yu Wang
(74) *Attorney, Agent, or Firm* — Duane Morris LLP; Gregory M. Lefkowitz; Jason M. Nolan

(57) ABSTRACT

A pH-responsive fusion peptide according to the present disclosure, containing a cell-penetrating peptide exhibiting a positive charge, which contains 2-15 arginine residues, and a β-sheet-forming segment, experiences structural change depending on pH change. Due to the structural change, the anti-prion activity and cytotoxicity of the fusion peptide can be controlled as desired.

10 Claims, 16 Drawing Sheets

Specification includes a Sequence Listing.

INTRACELLULAR PH-RESPONSIVE FUSION PEPTIDE AND PHARMACEUTICAL COMPOSITION FOR REDUCING ABNORMAL PRION PROTEIN AGGREGATION OR MISFOLDING

CROSS-REFERENCE TO RELATED APPLICATIONS

This application claims, under 35 U.S.C. § 119, the priority of Korean Patent Application No. 10-2016-0161767 filed on Nov. 30, 2016 in the Korean Intellectual Property Office, the disclosure of which is incorporated herein by reference in its entirety.

TECHNICAL FIELD

The present disclosure relates to an intracellular pH-responsive fusion peptide and a pharmaceutical composition for preventing or treating a disease associated with abnormal protein aggregation or misfolding containing the same as an active ingredient.

BACKGROUND

Amyloids are protein aggregates that form fibrous deposits of proteins mainly having a cross-beta sheet secondary structure, which exhibit birefringence or fluorescence when stained with amyloid-specific dyes such as Congo red and thioflavin T and are insoluble in aqueous solutions (Murphy, R. M., *Annu. Rev. Biomed. Eng.*, 4: 155, 2002). Basically, the amyloids are formed as a result of abnormal folding which leads to change in secondary and tertiary structures without change in the primary structure of proteins. The amyloid deposits induce tissue damage. The amyloids are associated with many diseases including Alzheimer's disease, prion-related encephalopathy, spongiform encephalopathy, Parkinson's disease, primary systemic amyloidosis, type 2 diabetes, familial amyloidosis and light-chain amyloidosis.

The amyloids are studied extensively only recently and there have been consistent researches on the abnormal folding of amyloid proteins and their cytotoxicity in order to elucidate the relationship between the deposition of amyloid proteins and neurodegenerative diseases. However, drugs for treating such diseases as Alzheimer's disease or prion disease have not been developed yet.

The existing drug development method is not applicable to the development of drugs for treating the amyloid-associated diseases caused by protein misfolding because of the absence of distinct recognition sites or binding pockets in amyloid proteins.

Although inhibitors have been developed based on the mechanisms of amyloid aggregation, e.g., increase of amyloid beta by SUMO1 (patent document 1), these methods are effective for single molecular species only.

The inventors of the present disclosure have made efforts to develop an inhibitor of protein misfolding leading to various amyloid aggregates or prions by using a self-assembled peptide nanostructure and have completed the present disclosure.

REFERENCES OF THE RELATED ART

Patent Document

Patent document 1. Korean Patent Publication No. 10-2015-0146181

SUMMARY

The present disclosure is directed to providing a fusion peptide which hardly exhibits cytotoxicity and anti-prion activity under an extracellular neutral pH condition and, upon uptake into a cell by endocytosis, forms a vesicular nanostructure having a pharmacological effect through structural change under the acidic condition of endosomes and lysosomes.

The present disclosure is also directed to providing a pharmaceutical composition for preventing or treating a disease associated with abnormal protein aggregation or misfolding, which contains the fusion peptide as an active ingredient.

In an aspect, the present disclosure provides a fusion peptide containing: a cell-penetrating peptide exhibiting a positive charge, which contains 2-15 arginine residues; and a β-sheet-forming segment represented by Chemical Formula 1:

$$-(-X_1-X_2-X_3-X_4-)_n- \qquad \text{[Chemical Formula 1]}$$

wherein
each of $X_1$ and $X_3$, which are identical or different from each other, is independently a hydrophobic aromatic amino acid residue,
$X_2$ is an amino acid residue exhibiting a positive charge;
$X_4$ is an amino acid residue exhibiting a negative charge; and
n is an integer from 1 to 10.

In Chemical Formula 1, $X_1$ and $X_3$ may be identical and selected from phenylalanine or tryptophan.

In Chemical Formula 1, $X_2$ and $X_4$ may be different from each other and, if $X_2$ is lysine, $X_4$ may be aspartic acid or glutamic acid.

The cell-penetrating peptide exhibiting a positive charge may be a Tat peptide or an oligoarginine peptide consisting of 2-15 arginine residues.

The fusion peptide may further contain a linker.

Most specifically, the fusion peptide may be represented by one of SEQ ID NOS 1 to 12.

The fusion peptide may form a nanostructure through self-assembly between fusion peptides via hydrophobic interaction and electrostatic binding of the β-sheet-forming segment under an acidic condition (pH 2-5.5).

The nanostructure may have a vesicular tertiary structure.

The fusion peptide may form a nanostructure having an amyloid fibril-type tertiary structure through self-assembly between fusion peptides via hydrophobic interaction and electrostatic binding of the β-sheet-forming segment under a condition of pH 9.0-12 and the fibrillar nanostructure may be stable regardless of pH change.

In another aspect, the present disclosure provides a pharmaceutical composition for preventing or treating a disease associated with abnormal protein aggregation or misfolding, which contains the fusion peptide.

The disease associated with abnormal protein aggregation or misfolding may be selected from a group consisting of Parkinson's disease, Huntington's disease, amyotrophic lateral sclerosis, polyglutamine expansion disease, spinocerebellar ataxia, spinal and bulbar muscular atrophy, tauopathy, dystonia, serpin deficiency, cirrhosis, type 2 diabetes, primary systemic amyloidosis, secondary systemic amyloidosis, frontotemporal dementia, senile systemic amyloidosis, familial amyloid polyneuropathy, hereditary cerebral amyloid angiopathy, hemodialysis-associated amyloidosis, age-related macular degeneration, Alzheimer's disease, radiotherapy-induced dementia, axon injury, acute cortical spreading depression, alpha-synucleinopathy, brain ischemia, permanent focal cerebral ischemia, peripheral nerve regeneration, post-status epilepticus model, spinal cord injury, sporadic amyotrophic lateral sclerosis and a prion disease such as Creutzfeldt-Jakob disease, spongiform encephalopathy and transmissible spongiform encephalopathy.

The disease associated with abnormal protein aggregation or misfolding may be dementia or mad cow disease.

The composition may form a vesicular nanostructure and exhibit increased anti-prion activity and cytotoxicity under an intracellular uptake condition of pH 2.0-6.0.

The pH-responsive fusion peptide according to the present disclosure exhibits structural change in response to pH change due to the cell-penetrating peptide exhibiting a positive charge, which contains 2-15 arginine residues, and the β-sheet-forming segment. The anti-prion activity and cytotoxicity of the fusion peptide can be controlled through the structural change.

That is to say, because the fusion peptide of the present disclosure, upon uptake into an endosome or a lysosome of a cell by endocytosis, is self-assembled into a vesicular nanostructure having anti-prion activity under an acidic condition of the endosome or the lysosome, it may prevent a prion protein ($PrP^C$) existing in the endosome or the lysosome from being converted to an infectious prion protein ($PrP^{SC}$) or being aggregated. Alternatively, it may interact with an infectious prion protein ($PrP^{SC}$) in the endosome or the lysosome, inhibiting $PrP^{SC}$ aggregation Accordingly, the fusion peptide of the present disclosure may prevent or treat a disease associated with abnormal aggregation or misfolding of proteins existing in the endosome or the lysosome because it does not exhibit anti-prion activity under an extracellular neutral condition but exhibits the activity upon uptake into a cell through structural change in response to pH change.

BRIEF DESCRIPTION OF DRAWINGS

FIG. 1 and FIGS. 2A to 2B show the mechanism of a fusion peptide according to the present disclosure.

FIG. 3 shows a western blot result of $PrP^{SC}$ having resistance to proteinase K in ScN2a cells treated with a fusion peptide prepared in Example 1 or Example 2 or with a single-molecule peptide prepared in Comparative Example 1.

FIG. 4 shows a circular dichroism analysis of a fusion peptide prepared in Example 1 or Example 2 or a single-molecule peptide prepared in Comparative Example 1 in a phosphate buffer solution at pH 7.4 and 25° C. for identification of the secondary structure of the peptide.

FIG. 5 shows a circular dichroism analysis of a fusion peptide prepared in Example 3 in a phosphate buffer solution at pH 7.4 and 25° C. for identification of the secondary structure of the peptide.

FIG. 6 shows a circular dichroism analysis of a fusion peptide prepared in Example 3 after pH is changed from 7.4 to 11.

FIG. 7 shows a circular dichroism analysis of a fusion peptide prepared in Example 3 after pH is changed from 7.4 to 11 and then again to 7.4.

FIG. 8 shows a western blot result of $PrP^{SC}$ having resistance to proteinase K in ScN2a cells treated with a peptide prepared in Example 3 ($R_{12}$-β), Comparative Example 2 ($R_{12}$) or Comparative Example 3 ($R_{60}$-polymer). The numbers on the top denote the concentration (nM) of the corresponding fusion peptide.

FIG. 9 shows a relative $PrP^{SC}$ level determined from the result of FIG. 8 through density measurement.

FIG. 10 shows a cytotoxicity analysis of a peptide synthesized in Example 3 ($R_{12}$-β), Comparative Example 2 ($R_{12}$) or Comparative Example 3 ($R_{60}$-polymer) for ScN2a cells.

FIGS. 11A-11D show negative-staining TEM images of a fusion peptide of Example 3, acquired to investigate the molecular state of the fusion peptide at a physiological salt concentration (150 mM NaCl) depending on pH change, at pH 3 (FIG. 11A), pH 5 (FIG. 11B), pH 7 (FIG. 11C) and pH 11 (FIG. 11D). The pH was adjusted using HCl or NaOH. The scale bar represents 1 μm.

FIGS. 12A-12C show AFM images of a fusion peptide of Example 3, acquired to investigate the molecular state of the fusion peptide at a physiological salt concentration (150 mM NaCl) depending on pH change, at pH 3 (FIG. 12A), pH 7 (FIG. 12B) and pH 11 (FIG. 12C).

FIG. 13 shows an AFM image of a fusion peptide of Example 3 self-assembled into a vesicle at pH 3 and its height (nm) with respect to width (nm) measured therefrom.

FIG. 14 shows a result of measuring the zeta potential of a fusion peptide of Example 3 depending on pH. The pH was adjusted using HCl or NaOH and the data are represented as mean±standard deviation (n=3).

FIG. 15 shows a result of measuring the zeta potential of a fusion peptide of Example 3 when pH was changed from 7 to 5 (green) and when pH was changed sequentially from 11 to 7 to 5 and then to 3 (blue). The pH was adjusted using HCl or NaOH and the data are represented as mean±standard deviation (n=3).

FIG. 16 shows transmission electron microscopic images of ScN2a cells treated with $R_{12}$-β UNS of Example 3, which did not form a nanostructure, at pH 7. The arrows indicate $R_{12}$-β vesicles.

FIG. 17 shows the MALDI-TOF mass spectrum of a fusion peptide of Example 4 (A=0.066, ε=1146, DF=2 C=115 μM (1 mL), $M.W._{cal}$=4147 g/mol, $M.W._{meas.}$=4165.288 g/mol).

FIG. 18 shows the MALDI-TOF mass spectrum of a fusion peptide of Example 5 (A=0.163, ε=1146, DF=2 C=284 μM (1 mL), $M.W._{cal}$=4303 g/mol, $M.W._{meas.}$=4319.148 g/mol).

FIG. 19 and FIG. 20 show the AFM images of the fusion peptide of Example 4 at pH 3 acquired to investigate whether the fusion peptide of Example 4 forms a vesicular nanostructure under physiological salt concentration (150 mM NaCl) and strongly acidic (pH 3) conditions. FIG. 19 is a phase image and FIG. 20 is a height image.

FIG. 21 shows the western blot result for the $PrP^{SC}$ having resistance to proteinase K in the ScN2a cells treated with the fusion peptide of Example 4 ($R_{14}$-β UNS).

FIG. 22 shows the western blot result for the $PrP^{SC}$ having resistance to proteinase K in the ScN2a cells treated with the fusion peptide of Example 5 ($R_{15}$-β UNS) In FIGS. 21 and 22, the numbers below $R_{14}$-β UNS and $R_{15}$-β UNS indicate the concentration (nM) of the fusion peptide.

DETAILED DESCRIPTION OF EMBODIMENTS

Hereinafter, various aspects and exemplary embodiments of the present disclosure are described in more detail.

In general, it is known that protein misfolding not only leads to the loss of the normal protein function but also causes toxicity due to accumulation of abnormal proteins in cells, thereby causing various diseases such as Alzheimer's disease, prion disease, Parkinson's disease, Huntington's disease, Lou Gehrig's disease, cancer, cystic fibrosis and type 2 diabetes. Through researches on protein misfolding, it was known that anti-amyloid compounds such as Congo red, etc. are effective in preventing fibril formation caused by protein misfolding. However, there are limitations in that they are highly toxic, cannot prevent the transport of misfolded proteins and, above all, merely prevent fibril formation of specific proteins rather than preventing protein misfolding.

In order to solve these problems, the present disclosure is directed to providing a fusion peptide capable of preventing formation of misfolded proteins by inhibiting protein misfolding or aggregation in the endosome and the lysosome of a cell before the protein synthesized in the cell is released out of the cell.

In particular, because the fusion peptide according to the present disclosure exhibits remarkably low cytotoxicity and hardly exhibits anti-prion activity under an extracellular neutral condition, it can be used safely for humans.

Upon uptake into the endosome and the lysosome of a cell by endocytosis, the fusion peptide is exposed to the weakly acidic condition of the endosome and the lysosome and is self-assembled into a vesicular nanostructure via hydrophobic interaction and electrostatic binding. As a result, the anti-prion activity is increased. Cytoplasmic vesicles such as the endosome or the lysosome are the intracellular locations where misfolding of normal prion proteins to pathogenic prion proteins is likely to occur.

Accordingly, the fusion peptide according to the present disclosure provides an effect of preventing or treating a disease associated with protein misfolding or aggregation by self-assembling into a vesicular nanostructure having anti-prion activity specifically and selectively at the intracellular location (endosome or lysosome) by preventing protein misfolding or aggregation.

In addition, it was confirmed from experiments on cells that the fusion peptide according to the present disclosure significantly inhibits the generation or accumulation of pathogenic prion proteins ($PrP^{SC}$) without affecting the growth of the cells.

An aspect of the present disclosure relates to a fusion peptide containing: a cell-penetrating peptide exhibiting a positive charge, which contains 2-15 arginine residues; and a β-sheet-forming segment represented by Chemical Formula 1:

$$-(-X_1-X_2-X_3-X_4-)_n- \quad \text{[Chemical Formula 1]}$$

wherein each of $X_1$ and $X_3$, which are identical or different from each other, is independently a hydrophobic aromatic amino acid residue, $X_2$ is an amino acid residue exhibiting a positive charge;

$X_4$ is an amino acid residue exhibiting a negative charge; and n is an integer from 1 to 10.

In an exemplary embodiment of the present disclosure, the cell-penetrating peptide exhibiting a positive charge, which contains 2-15 arginine residues, is an arginine-rich hydrophilic segment which can be transported into a cell by endocytosis without disrupting the cell. However, because the cell-penetrating peptide exhibiting a positive charge has cytotoxicity in proportion to the magnitude of the positive charge, sufficient pharmacological effect cannot be achieved only with the cell-penetrating peptide exhibiting a positive charge.

In addition, the cell-penetrating peptide exhibiting a positive charge may be a Tat peptide or an oligoarginine peptide consisting of 2-15 arginine residues. Specifically, the cell-penetrating peptide may be an oligoarginine peptide consisting of 6-15 arginine residues.

It is because, if the cell-penetrating peptide consists of 5 or less arginine residues or contains another residue having a positive charge in addition to the arginine residues, it may not be self-assembled in response to pH change to form a stable structure. Accordingly, it is preferred that the cell-penetrating peptide consists of at least 5 arginine residue. Meanwhile, if the cell-penetrating peptide consists of more than 15 arginine residues, self-assembly may not occur as desired under a weakly acidic condition because electrostatic repulsion is much stronger than the attraction between the β-sheet-forming segments owing to excessively high charge.

For example, the cell-penetrating peptide of the present disclosure may be represented by Chemical Formula 2:

$$-[Arg]_m- \quad \text{[Chemical Formula 2]}$$

wherein m is an integer from 6 to 15.

The cell-penetrating peptide consisting of arginine residues binds to the β-sheet-forming segment represented by Chemical Formula 1 and forms a block copolypeptide-type fusion peptide that can be self-assembled via β-sheet interactions (electrostatic binding and hydrophobic interaction) in response to pH change. Its structure is shown in FIGS. 2A and 2B.

The β-sheet-forming segment represented by Chemical Formula 1 consists of a hydrophobic amino acid residue having an aromatic functional group and an amino acid residue exhibiting a positive charge or a negative charge, which are linked alternatively. A specific example is as follows.

$$-(-X_1-X_2-X_3-X_4-)_n- \quad \text{[Chemical Formula 1]}$$

wherein each of $X_1$ and $X_3$, which are identical or different from each other, is independently a hydrophobic aromatic amino acid residue, $X_2$ is an amino acid residue exhibiting a positive charge;

$X_4$ is an amino acid residue exhibiting a negative charge; and n is an integer from 1 to 10.

The β-sheet-forming segment is not particularly limited if it is one formed as a hydrophobic amino acid having an aromatic functional group and an amino acid residue exhibiting a charge are linked alternatively. A more detailed description is given below.

In order to achieve the effect described above, the fusion peptide according to the present disclosure should exist as an unstructured form such as a unimolecular form under a neutral condition (pH 6.0-9.0) and should be converted to a vesicular nanostructure under the weakly acidic condition (pH 2-5.5) of the endosome or the lysosome in a cell via a specific reaction (see FIG. 1 and FIGS. 2A to 2B).

In FIG. 1 and FIGS. 2A to 2B, the yellow arrows indicate the β-sheet-forming segments and the red cones indicate the cell-penetrating peptides exhibiting a positive charge.

Upon exposure to a weakly acidic condition, at least one of the fusion peptide is self-assembled via hydrophobic interaction and electrostatic binding to form a vesicular nanostructure. Specifically, the β-sheet-forming segment of a fusion peptide is bound to the β-sheet-forming segment of another fusion peptide via hydrophobic interaction and electrostatic binding in an antiparallel fashion and the bound fusion peptide unit structures (see ② in FIG. 1) are aligned and arranged according to their hydrophobicity and hydrophilicity to form a hollow particulate structure, i.e., a vesicular nanostructure. The cell-penetrating peptide exhibiting a positive charge and the β-sheet-forming segment do not form a vesicular nanostructure under a neutral condition (pH 6.0-9.0) and is self-assembled into a vesicular nanostructure only under an acidic or weakly acidic condition (pH 2-5.5).

Under a basic condition (pH 10-12), the fusion peptide can self-assemble to form a specific form of nanostructure, which is a fibrillar nanostructure like amyloids. Such a nanostructure does not exhibit an activity of preventing or inhibiting protein misfolding or aggregation even after uptake into the endosome or the lysosome of a cell.

The fibrillar nanostructure has an irreversible structure which is not changed despite pH change.

In the binding between the at least one β-sheet-forming segment according to the present disclosure, "antiparallel" means that, when β-sheet-forming segments are fixed by hydrogen bonding, one of the β-sheet-forming segments is aligned in a direction from the N terminal toward the C terminal (N→C) and the other β-sheet-forming segment bound to the β-sheet-forming segment is aligned in the opposite direction (C←N) (see the yellow arrows in FIG. 1).

The β-sheet-forming segment represented by Chemical Formula 1 according to an exemplary embodiment of the present disclosure may form hydrophobic interaction and electrostatic binding with the neighboring β-sheet-forming segment as described above.

Specifically, the hydrophobic aromatic amino acid residue may be phenylalanine (Phe) or tryptophan (Trp), the amino acid residue exhibiting a positive charge may be arginine (Arg), histidine (His) or lysine (Lys) and the amino acid residue exhibiting a negative charge may be aspartic acid (Asp) or glutamic acid (Glu).

When the at least one fusion peptide are bound, the binding between β-sheet-forming segments of one fusion peptide and another neighboring fusion peptide may be formed by hydrophobic interaction of phenylalanine or tryptophan and by electrostatic binding of the positively charged ammonium ion of the amino acid residue exhibiting a positive charge and the negatively charged carboxylate ion of the amino acid residue exhibiting a negative charge. The binding is the strongest at pH 4.5-5.5.

In an exemplary embodiment of the present disclosure, in Chemical Formula 1, $X_1$ and $X_3$ may be identical and selected from phenylalanine or tryptophan.

Specifically, for balanced attraction and repulsion with the cell-penetrating peptide exhibiting a positive charge, in Chemical Formula 1, $X_2$ and $X_4$ may be different from each other and, if $X_2$ is lysine, $X_4$ may be aspartic acid or glutamic acid.

The cell-penetrating peptide exhibiting a positive charge and the β-sheet-forming segment may be bound either directly or via a linker.

The linker may be a glycine polymer ($(G)_n$), a glycine-serine polymer (e.g., $(GS)_n$, $(GSGS)_n$ or $(GGGS)_n$, where n is an integer of at least 1), a glycine-alanine polymer, an alanine-serine polymer, a tether for the Shaker potassium channel or a flexible linker such as ahx. Glycine is preferred to alanine since glycine can access phi-psi space more effectively than alanine and is less restricted than amino acid residues having longer side chains. And, because serine is hydrophilic and can dissolve the spherical glycine chain, a flexible linker consisting of glycine and serine is preferred the most. ahx refers to 6-aminohexanoic acid ($(CH_2)_6$—$NH_2$).

The fusion peptide may be one represented by one of SEQ ID NOS 1 to 12.

FIGS. 2A and 2B show the mechanism of the fusion peptide according to the present disclosure.

As seen from FIGS. 2A and 2B, under an acidic condition (pH 2-5.5), the glutamic acid residue is protonated and the carboxylate anion is converted to more hydrophobic carboxylic acid. As a result, a vesicular nanostructure is formed through self-assembly. Specifically, the fusion peptide is converted to the vesicular nanostructure as the hydrophobicity of the β-sheet is increased and, as a result, the volume of the hydrophobic block is increased.

That is to say, when the fusion peptide according to the present disclosure is administered into a cell in vivo or in vitro, if the fusion peptide according to the present disclosure is administered at pH 7.4 or lower, the fusion peptide is not structured or forms an unstable aggregate, thereby exhibiting low cytotoxicity. The fusion peptide not structured or forming an unstable aggregate is introduced into the cell via endocytosis. Due to pH decrease (early endosome: pH 6.0-6.5, late endosome and lysosome: pH 4.5-5.5) as a result of the endocytosis, the fusion peptide is self-assembled to form the vesicular nanostructure. It was confirmed from experiments that will be described below that the fusion peptide of the present disclosure is self-assembled in the cell to form a vesicular nanostructure. When the fusion peptide is converted to the vesicular nanostructure, it exhibits 4.5 times higher anti-prion activity as compared to a polymer consisting only of arginine residues due to increased effective molecular weight and charge density.

The conversion of prion and the maturation of $PrP^{SC}$ associated with various diseases induced by protein misfolding occur inside the endosome/lysosome. Because the fusion peptide according to the present disclosure forms a vesicular nanostructure in the cell (particularly inside the endosome and the lysosome), it exhibits low cytotoxicity and low anti-prion activity in cellulo but exhibits strong anti-prion activity inside the endosome and the lysosome.

In contrast, if the fusion peptide is treated with a basic condition (pH 10-12), it is self-assembled into a nanostructure similar to an amyloid. Therefore, it is resistant to change of the nanostructure during endocytosis and exhibits moderate cytotoxicity and anti-prion activity both inside and outside of a living cell. The amyloid-like fibrillar nanostructure is an irreversible structure and is structurally stable against pH change.

As seen from FIG. 2A, as the fusion peptide according to the present disclosure (the red color indicates the cell-penetrating peptide exhibiting a positive charge and the yellow arrow indicates the β-sheet-forming segment) is self-assembled, the β-sheet portions are arranged in an antiparallel fashion and the resulting structural unit forms the surface of a vesicle. The cell-penetrating peptide exhibiting a positive charge, consisting of arginine residues, displayed in red color, is arranged outward and the β-sheet is located inside the membrane. This molecular arrangement maximizes molecular arrangement density and charge density.

As described above, because the fusion peptide does not exhibit anti-prion activity and has little cytotoxicity under an extracellular condition, side effects occurring therefrom can be avoided.

In addition, the fusion peptide is very effective because it exhibits the effect of inhibiting and preventing protein misfolding or abnormal protein aggregation even though it does not contain an additional drug. Once synthesized, the fusion peptide is specifically and selectively prepared into a vesicular nanostructure through self-assembly under a weakly acidic condition. The resulting vesicular nanostructure is in the form of a hollow particle with a bilayered membrane, with the cell-penetrating peptide exhibiting a positive charge exposed outward and the β-sheet-forming segment located inside the membrane. This type of nanostructure exhibits remarkably higher anti-prion activity as compared to a peptide or a peptide polymer consisting only of arginine residues.

The fusion peptide of the present disclosure has a zeta potential of +38 to +40 mV under an acidic or weakly acidic condition (pH 2-5.5), +22 to +26 mV under a neutral condition (pH 6.0-9.0) and +28 to +32 mV under a basic condition (pH 10.0-12.0).

Another aspect of the present disclosure relates to a pharmaceutical composition for preventing or treating a disease associated with abnormal protein aggregation or misfolding, which contains the fusion peptide.

The pharmaceutical composition for preventing or treating a disease associated with abnormal protein aggregation or misfolding of the present disclosure contains a fusion peptide containing: a cell-penetrating peptide exhibiting a positive charge, which contains 2-15 arginine residues; and a β-sheet-forming segment represented by Chemical Formula 1 as an active ingredient.

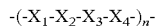   [Chemical Formula 1]

wherein
each of $X_1$ and $X_3$, which are identical or different from each other, is independently a hydrophobic aromatic amino acid residue,
$X_2$ is an amino acid residue exhibiting a positive charge;
$X_4$ is an amino acid residue exhibiting a negative charge; and
n is an integer from 1 to 10.

In the followings, the same contents as described above with respect to the fusion peptide will be omitted.

The disease associated with abnormal protein aggregation or misfolding includes not only a disease or disorder caused by the misfolding or aggregation of a prion protein, such as mad cow disease, but also diseases caused by the aggregation of other proteins (e.g., β-amyloid and tau protein causing Alzheimer's disease, α-synuclein causing Parkinson's disease, TDP-43 protein associated with frontotemporal lobar degeneration and amyotrophic lateral sclerosis, etc.). Specifically, it may be selected from a group consisting of Parkinson's disease, Huntington's disease, amyotrophic lateral sclerosis, polyglutamine expansion disease, spinocerebellar ataxia, spinal and bulbar muscular atrophy, tauopathy, dystonia, serpin deficiency, cirrhosis, type 2 diabetes, primary systemic amyloidosis, secondary systemic amyloidosis, frontotemporal dementia, senile systemic amyloidosis, familial amyloid polyneuropathy, hereditary cerebral amyloid angiopathy, hemodialysis-associated amyloidosis, age-related macular degeneration, Alzheimer's disease, radiotherapy-induced dementia, axon injury, acute cortical spreading depression, alpha-synucleinopathy, human kuru, brain ischemia, permanent focal cerebral ischemia, peripheral nerve regeneration, post-status epilepticus model, spinal cord injury, sporadic amyotrophic lateral sclerosis and a prion disease such as Creutzfeldt-Jakob disease (CJD), variant Creutzfeldt-Jakob disease (vCJD), iatrogenic Creutzfeldt-Jakob disease (iCJD), familial Creutzfeldt-Jakob disease (fCJD), sporadic Creutzfeldt-Jakob disease (sCJD), Gerstmann-Strässler-Scheinker syndrome (GSS), fatal familial insomnia (FFI), sporadic fatal insomnia (sFI), spongiform encephalopathy and transmissible spongiform encephalopathy.

More specifically, the disease associated with abnormal protein aggregation or misfolding may be a prion disease. The prion disease may include human kuru, brain ischemia, permanent focal cerebral ischemia, peripheral nerve regeneration, post-status epilepticus model, spinal cord injury, sporadic amyotrophic lateral sclerosis, Creutzfeldt-Jakob disease (CJD), variant Creutzfeldt-Jakob disease (vCJD), iatrogenic Creutzfeldt-Jakob disease (iCJD), familial Creutzfeldt-Jakob disease (fCJD), sporadic Creutzfeldt-Jakob disease (sCJD), Gerstmann-Strässler-Scheinker syndrome (GSS), fatal familial insomnia (FFI), sporadic fatal insomnia (sFI), spongiform encephalopathy, transmissible spongiform encephalopathy, Alzheimer's disease, mad cow disease, etc.

Prions are infectious agents entirely different from the existing pathogens. They are much smaller than common viruses and cause infectious diseases without the use of nucleic acids. It is known that prion infections in animals including human cause neurodegenerative diseases by destroying brain neurons. The disease induced by a prion protein is caused by the infectious form isoform of prion protein ($PrP^C$) which has been converted from the normal prion protein ($PrP^{SC}$).

The fusion peptide of the present disclosure does not exhibit cytotoxicity and anti-prion activity under an extracellular condition but, upon uptake into the endosome or the lysosome of a cell by endocytosis, is converted to a vesicular nanostructure and exhibits superior anti-prion activity. That is to say, the nanostructure formed from the fusion peptide in the endosome or the lysosome of the cell effectively inhibits and prevents abnormal aggregation or deforming of the prion protein, thereby effectively preventing the formation of misfolded prion proteins.

Accordingly, the fusion peptide of the present disclosure can be usefully used to prevent or treat a disease caused by abnormal aggregation or misfolding of a protein, particularly the prion disease, and can be safely used for humans.

In particular, the fusion peptide of the present disclosure may prevent or treat a disease caused by abnormal aggregation or misfolding of the prion protein in the endosome or the lysosome.

The composition may be introduced into the endosome or the lysosome of a cell by endocytosis and form a vesicular nanostructure under the pH 2.0-5.5 condition of the endosome or the lysosome. As a result, the anti-prion activity may be increase.

In the present, the term 'containing as an active ingredient' means that the fusion peptide of the present disclosure is contained in an amount sufficient to prevent a disease associated with abnormal protein aggregation or misfolding, particularly a disease caused by abnormal aggregation or misfolding of the prion protein in the endosome or the lysosome existing in a cell (specifically, Alzheimer's disease or Creutzfeldt-Jakob disease).

The pharmaceutical composition for preventing or treating a disease associated with abnormal protein aggregation or misfolding of the present disclosure may contain the fusion peptide at a concentration of 0.001-2000 μg/mL, specifically 0.1-1000 μg/mL, although not being limited thereto. Because the fusion peptide exhibits low cytotoxicity in human even when administered in an excess amount, the upper limit of the concentration of the fusion peptide in the composition of the present disclosure may be selected adequately by those skilled in the art.

In another exemplary embodiment, the pharmaceutical composition for preventing or treating a disease associated with abnormal protein aggregation or misfolding may be delivered to a human or other mammals having a disease condition or symptom by injection or other methods (e.g., implantation, insertion into the body cavity or other available space, coating on the surface of body tissue or an implantable apparatus). In particular, the composition may be delivered parenterally. The term 'parenterally' means intramuscularly, intraperitoneally, intraabdominally, subcutaneously, intravenously or intraarterially. Therefore, the composition of the present disclosure may be typically prepared as an injectable formulation.

The injectable composition of the present disclosure may be injected or inserted into a human or other mammals by any suitable method, specifically by injection through a hypodermic needle.

For example, it may be administered intraarterially, intravenously, intraurogenitally, subcutaneously, intramuscularly, intracranially, intrapericardially, intrapleurally or into the body cavity or other available space by injection or other methods. Also, it may be introduced through a catheter or a syringe, for example, intraarticularly during arthroscopy or intraurogenitally, intravascularly, intrapalatally, intrapleurally or into the body cavity or other available space during operation, surgery, diagnosis or intervention.

The administration dosage of the composition will vary depending on the treated disease or disorder to be treated and its severity. Further, it is to be understood that the administration dosage for a particular subject can be adjusted according to individual needs or discretion of a diagnoser or a prescriber. In-vivo administration can be made based on the studies conducted on cells cultured in vitro or in-vivo animal models.

The pharmaceutical composition according to the present disclosure may further contain a commonly used adequate carrier, excipient or a diluent and may be prepared into an oral formulation such as a powder, a granule, a tablet, a capsule, a suspension, an emulsion, a syrup, an aerosol, etc., a formulation for external application, a suppository or a sterile injectable solution according to commonly employed methods.

Examples of the carrier, excipient or diluent that may be contained in the composition of the present disclosure include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil.

For formulation, a commonly used diluent or excipient such as a filler, an extender, a binder, a wetting agent, a disintegrant, a surfactant, etc. is used. Solid formulations for oral administration include a tablet, a pill, a powder, a granule, a capsule, etc. The solid formulation is prepared by mixing the pharmaceutical composition of the present disclosure with at least one excipient, e.g., starch, calcium carbonate, sucrose, lactose, gelatin, etc. In addition to the simple excipient, a lubricant such as magnesium stearate and talc is also used. Liquid formulations for oral administration include a suspension, a solution for internal use, an emulsion, a syrup, etc. In addition to a commonly used simple diluent such as water and liquid paraffin, various excipients, e.g., a wetting agent, a sweetener, an aromatic, a preservative, etc. may be contained. Formulations for parenteral administration include a sterilized aqueous solution, a non-aqueous formulation, a suspension, an emulsion, a freeze-dried formulation and a suppository. The non-aqueous formulation or suspension may contain propylene glycol, polyethylene glycol, vegetable oil such as olive oil, an injectable ester such as ethyl oleate, etc. As a base of the suppository, witepsol, macrogol, Tween 61, cocoa butter, laurin butter, glycerogelatin, etc. may be used.

The composition of the present disclosure may be administered orally or parenterally. The parenteral administration may be made by any method and systemic administration or topical administration is possible. More specifically, it may be administered by systemic administration. Most specifically, it may be administered by intravenous administration.

The administration dosage of the composition of the present disclosure will vary depending on the patient's condition and body weight, severity of a disease, administration type, administration route and administration period and may be selected adequately by those skilled in the art. To achieve the desired effect, the composition of the present disclosure may be administered with a daily dosage of 0.0001-10 g/kg, specifically 0.001-8 mg/kg. However, the administration dosage does not limit the scope of the present disclosure by any means.

In the present disclosure, the term "prevention" means any action that prevents or delays abnormal aggregation or misfolding of proteins, particularly prion proteins existing in the endosome or the lysosome of a cell, by administering the pharmaceutical composition according to the present disclosure and the term "treatment" means any action that improves or advantageously changes the possibility of abnormal aggregation or misfolding of proteins, particularly prion proteins existing in the endosome or the lysosome of a cell, or the symptoms of an individual by administering the pharmaceutical composition.

In the present disclosure, the fusion peptide may be prepared into a powder form through an additional process such as distillation under reduced pressure, freeze-drying, spray drying, etc.

The fusion peptide of the present disclosure also includes a product that has been formulated for administration to animals only, such as a powder. Although experiments were conducted using the fusion peptide as described below, it will be expected by those skilled in the art that the desired effect can be achieved also with such a processed product of the fusion peptide.

Hereinafter, the present disclosure will be described in more detail through examples. However, the scope of the present disclosure is not reduced or limited by the following examples. It will be obvious that those of ordinary skill in the art can easily carry out the present disclosure for which experimental results are not specifically described on the basis of the disclosure of the present disclosure including the examples and that such modifications and changes belong to the scope of the present disclosure.

The experimental results presented below are only representative experimental results of the examples and comparative examples.

Cell Culturing

Cell culturing was conducted on a culture dish (diameter: 100 mm, Corning, USA) by subculturing with 4-5 day intervals. Experiments using prions were conducted in a BL-2 facility.

ScN2a cells were cultured according to methods described in the literature. In brief, ScN2a cells permanently infected with scrapie prions were grown in a glucose-rich (4.5 g/L) DMEM medium (Invitrogen, USA) containing 10% fetal bovine serum (FBS, USA), 1% penicillin-streptomycin (Invitrogen, USA) and 1% Glutamax (Invitrogen, USA). Then, the cells were incubated at 37° C. under a saturation humidity condition of 5% $CO_2$. The cells were subcultured on a culture dish (diameter: 100 mm, Corning, USA) with 4-5 day intervals. Experiments using prions were conducted in a BL-2 facility.

EXAMPLES 1-3

Synthesis of Self-Assembling Fusion Peptide

An Fmoc-amino acid and a coupling reagent were purchased from Novabiochem (Germany) and AnaSpec (USA), respectively. Other chemical reagents were purchased from Sigma-Aldrich (USA) and Merck (Germany).

Self-assembling peptides having the sequence identification numbers described in Table 1 were synthesized using the Rink Amide MBHA resin LL (Novabiochem, Germany) having a standard amino acid-protecting group according to the standard Fmoc protocol and the Triute peptide synthesizer (Protein Technologies, USA).

For cleavage from the resin and deprotection, the resin to which the synthesized peptide is bound was treated with a cleavage cocktail [trifluoroacetic acid (TFA)/triisopropylsilane (TIS)/water, (95:2.5:2.5)] for 3 hours, followed by trituration with tert-butyl methyl ether and purification by reverse-phase HPLC (water-acetonitrile containing 0.1% TFA).

A MALDI-TOF (matrix-assisted laser desorption/ionization time-of-flight) mass spectrometer (Microflex LRF20, Bruker, Germany) was used to determine the molecular weight of the peptide. α-Cyano-4-hydroxycinnamic acid (CHCA) was used as a matrix. The concentration of the synthesized peptide was spectrophotometrically determined in water/acetonitrile (1:1) from the molar extinction coefficient ($191 \text{ M}^{-1}\text{cm}^{-1}$) of phenylalanine at 257 nm.

Figure 17:
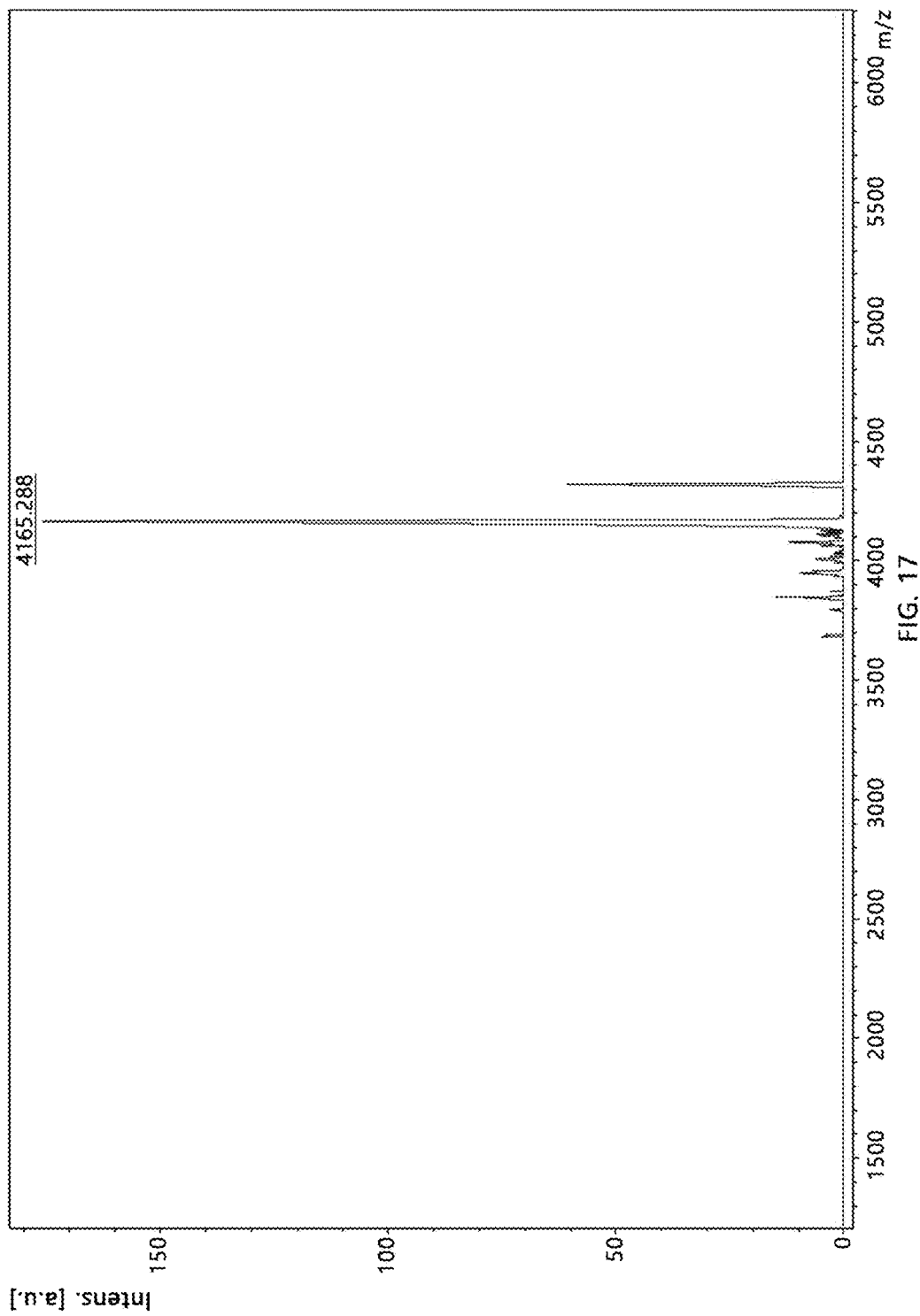
Figure 18:
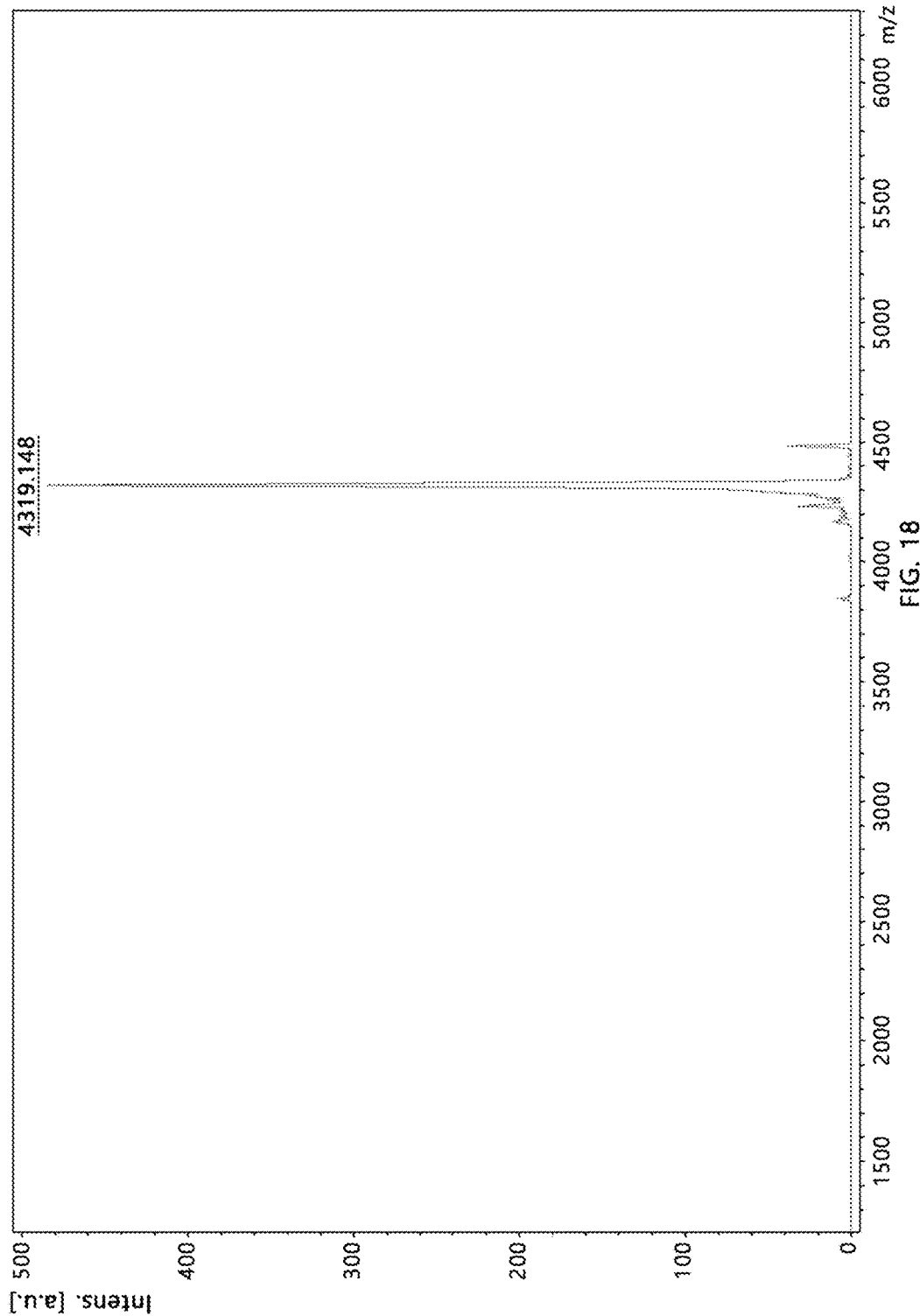

Fusion peptides that can self-assemble to nanostructures through β-sheet interactions were designed and synthesized as described in Table 1 by varying the charge density and length of the arginine-rich hydrophilic segment (The MALDI-TOF spectra for the fusion peptides of Examples 4 and 5 are shown in FIG. 17 and FIG. 18.).

TABLE 1

| | Fusion peptide | Sequence (N→C) |
|---|---|---|
| Example 1 | Tat-β (SEQ ID NO 13) | H-GRKKRRQRRRPPQ-GSGG-FKFEFKFEFKFE-NH$_2$ |
| Example 2 | R$_2$-β (SEQ ID NO 14) | H-RR-ahx-FKFEFKFEFKFE-NH$_2$ |
| Example 3 | R$_{12}$-β (SEQ ID NO 1) | H-RRRRRRRRRRRR-GSGG-FKFEFKFEFKFE-NH$_2$ |
| Example 4 | R$_{14}$-β (SEQ ID NO 3) | H-RRRRRRRRRRRRRR-GSGG-FKFEFKFEFKFE-NH$_2$ |
| Example 5 | R$_{15}$-β (SEQ ID NO 4) | H-RRRRRRRRRRRRRRR-GSGG-FKFEFKFEFKFE-NH$_2$ | ahx: ε-aminohexanoic acid

COMPARATIVE EXAMPLES 1-3

Synthesis of Single-molecule Peptide

Single-molecule peptides of Comparative Examples 1-3 having SEQ ID NOs: 15-17 were prepared in the same manner as in Example 1.

The R$_{60}$-polymer was purchased from Sigma-Aldrich (USA).

TABLE 2

| | Fusion peptide | Sequence (N→C) |
|---|---|---|
| Comparative Example 1 | Tat (SEQ ID NO 15) | H-ahx-GRKKRRQRRRPPQ-NH$_2$ |
| Comparative Example 2 | R$_{12}$ (SEQ ID NO 16) | H-RRRRRRRRRRRR-NH$_2$ |
| Comparative Example 3 | R$_{60}$ polymer (SEQ ID NO 17) | -(R)$_{60}$- | ahx: ε-aminohexanoic acid

TEST EXAMPLE 1

Measurement and Comparison of Anti-prion Activity of Fusion Peptide and Single-molecule Peptide For measurement and comparison of the anti-prion activity of the fusion peptides and single-molecule peptides, ScN2a cells were treated with the fusion peptides prepared in Examples 1-3 and the single-molecule peptides prepared in Comparative Examples 1-3 as described below and then the intracellular level of PrP$^{SC}$ was measured by western blot and circular dichroism (CD) analysis.

1) Cell Culturing

ScN2a cells were cultured according to methods described in the literature [Lee, Y. S. Self-assembly and nanotechnology: a force balance approach. (John Wiley & Sons, 2008); Stuart, M. A. et al. Emerging applications of stimuli-responsive polymer materials. *Nature Mater.* 9, 101-113 (2010)].

In brief, ScN2a cells permanently infected with scrapie prions were grown in a glucose-rich (4.5 g/L) DMEM medium (Invitrogen, USA). The DMEM medium was supplemented with 10% fetal bovine serum (FBS, USA), 1% penicillin-streptomycin (Invitrogen, USA) and 1% Glutamax (Invitrogen, USA). The cells were cultured at 37° C. under a saturation humidity condition of 5% CO$_2$. The cultured cells were subcultured on a culture dish (diameter: 100 mm, Corning, USA) with 4-5 day intervals. Experiments using prions were conducted in a BL-2 facility.

2) Incubation with Peptide

The cells cultured according to the literature [Lee, Y. S. Self-assembly and nanotechnology: a force balance approach. (John Wiley & Sons, 2008); Stuart, M. A. et al. Emerging applications of stimuli-responsive polymer materials. *Nature Mater.* 9, 101-113 (2010)] as described above were treated respectively with the fusion peptides of Examples 1-3 and the single-molecule peptides of Comparative Examples 1-3.

When the confluence reached 100%, the ScN2a cells were separated and grown on a culture dish (diameter: 100 mm, Corning, USA) from 2% confluence. As soon as the cells were attached on the surface of the culture dish (after about 4-6 hours), the peptide sample (one of the peptides of Examples 1-3 and Comparative Examples 1-3) was added to final peptide concentrations of 0-1000 nM and the cells were cultured for 6 days. On day 4, the culture medium was replaced with a fresh culture medium and the same peptide sample of the same amount.

3) Western Blot

For comparative analysis of the anti-prion activity of the peptides of Examples 1-3 and Comparative Examples 1-3, the $PrP^{SC}$ concentration of the ScN2a cells treated with each peptide was measured by western blot.

The western blot was conducted according to the literature [Stuart, M. A. et al. Emerging applications of stimuli-responsive polymer materials. *Nature Mater.* 9, 101-113 (2010)]. Specifically, the ScN2a cells treated with each peptide for 6 days were washed 2 times with cold PBS (Invitrogen, USA) and a cell lysate was prepared using 1 mL of a cell lysis buffer [20 mM Tris, pH 8.0; 150 mM sodium chloride, 0.5% Nonidet P-40, 0.5% sodium deoxycholate (Sigma-Aldrich, USA)]. A portion of the cell lysate was centrifuged to remove cell debris and proteins in the clear supernatant were quantitated using a bicinchoninic acid protein assay kit (Pierce, USA).

The remaining portion of the cell lysate (2 mg) was incubated with 20 μg/mL proteinase K (PK, Invitrogen, USA) at 37° C. for 1 hour and then phenylmethanesulfonyl fluoride (Sigma-Aldrich, USA) was added to the solution to a final concentration of 2 mM to terminate the enzyme reaction.

The reaction mixture was centrifuged at 16,000×g for 1 hour at 4° C. to obtain pellets containing PK-resistant $PrP^{Sc}$. The obtained pellets were dissolved in a 1× sample loading buffer (50 mM Tris-HCl, pH 6.8, 2% SDS, 10% glycerol, 2.5% 2-mercaptoethanol, 0.01% bromophenol blue) and then heated at 97° C. for 10 minutes. The heated sample was separated on a 12% SDS-polyacrylamide gel for 1.5 hours under a voltage of 120 V and the loaded protein sample present on the gel was electrophoresed to the Immobilon P PVDF membrane (EMD Millipore, Merck KGaA, Germany). Then, western blot was conducted using monoclonal anti-PrP antibody clones $5C6^4$ (acquired from G. Telling of Colorado State University) and secondary anti-mouse IgG-peroxidase conjugates (Pierce, Rockford, USA).

Figure 3:
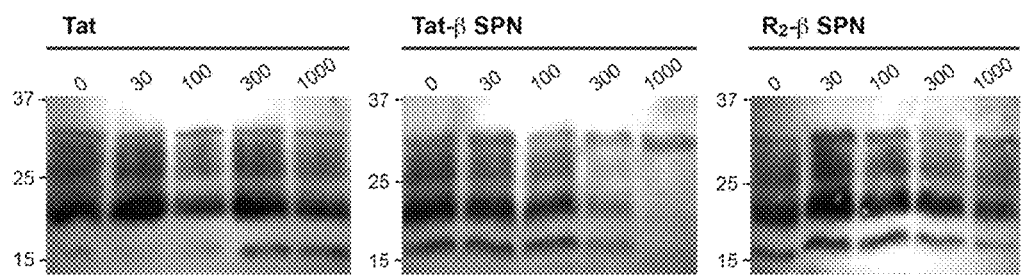

The $PrP^{Sc}$ band was visualized using the ECL Prime reagent (Amersham, GE Healthcare, USA). After obtaining images using the G:Box Chemi XR5 system (Syngene, UK), they were subjected to density analysis using the GeneTools software (Syngene, UK). The result is shown in FIG. 3.

4) Circular Dichroism (CD) Spectroscopy

CD spectra were recorded using the Chirascan circular dichroism spectrometer equipped with a Peltier temperature controller (Applied Photophysics, UK).

Figure 4:
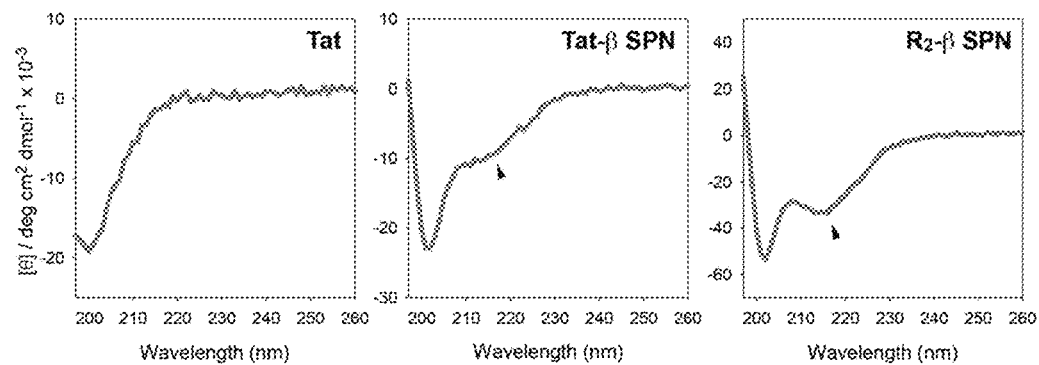

The CD spectra of the peptides were recorded at 190-260 nm using a cuvette with a pass length of 1 mm. The peptide concentration was 10-20 mM and the molar extinction coefficient was calculated per amino acid residue. The result is shown in FIG. 4.

FIG. 3 shows the western blot result of the $PrP^{SC}$ having resistance to proteinase K in the ScN2a cells treated with the fusion peptide prepared in Example 1 or Example 2 or with the single-molecule peptide prepared in Comparative Example 1.

From FIG. 3, it was confirmed that the fusion peptide prepared in Example 1 forms a nanoribbon-type nanostructure self-assembled via β-sheet interaction. That is to say, whereas the single-molecule peptide prepared in Comparative Example 1 (Tat peptide) does not exhibit anti-prion activity, the fusion peptide of Example 1 (Tat-β) is aggregated and self-assembled via β-sheet interaction to form the nanoribbon-type nanostructure exhibiting anti-prion activity.

In other words, it can be seen that, whereas the single-molecule peptide of Comparative Example 1 (Tat) does not show decrease in the $PrP^{SC}$ concentration at various concentrations, the fusion peptide of Example 1 (Tat-β) exhibits gradual decrease in the $PrP^{SC}$ concentration as its concentration is increased. That is to say, it can be seen that the fusion peptide of Example 1 has anti-prion activity. Specifically, it was confirmed that the fusion peptide of Example 1 exhibits the activity at concentrations of 100 nM or higher.

In addition, it was confirmed that the fusion peptide of Example 2 shows anti-prion activity, although weaker than that of the fusion peptide of Example 1.

FIG. 4 shows the circular dichroism analysis of the fusion peptide prepared in Example 1 or Example 2 or the single-molecule peptide prepared in Comparative Example 1 in a phosphate buffer solution at pH 7.4 and 25° C. for identification of the secondary structure of the peptides.

As seen from FIG. 4, it was confirmed that, whereas the single-molecule peptide of Comparative Example 1 is not structured, the fusion peptide of Example 1 is self-assembled to form a nanostructure via β-sheet interaction, as expected from the analysis result shown in FIG. 3. It was also confirmed that the fusion peptide of Example 2 is also self-assembled to form a nanoribbon-type nanostructure via β-sheet interaction.

The fusion peptide of Example 2 showed weaker anti-prion activity than the fusion peptide of Example 1, probably due to the difference in the number of arginine residues of the fusion peptides of Example 1 and Example 2. It is though that the prion inhibition activity is inversely proportional to the charge density on the surface of the self-assembled nanostructure and the increase in the effective molecular weight of the arginine-rich peptide during the self-assembly process leads to the formation of a stronger prion inhibitor.

TEST EXAMPLE 2

Structural Analysis of Fusion Peptide Synthesized in Example 3

Based on the result of Test Example 1, a fusion peptide of Example 3 (SEQ ID NO: 1) was designed to form a nanostructure with a high charge density. The secondary structure of the fusion peptide of Example 3 was analyzed by circular dichroism analysis as described in Test Example 1, 4) at pH 7.4. The result is shown in FIG. 5.

Figure 5:
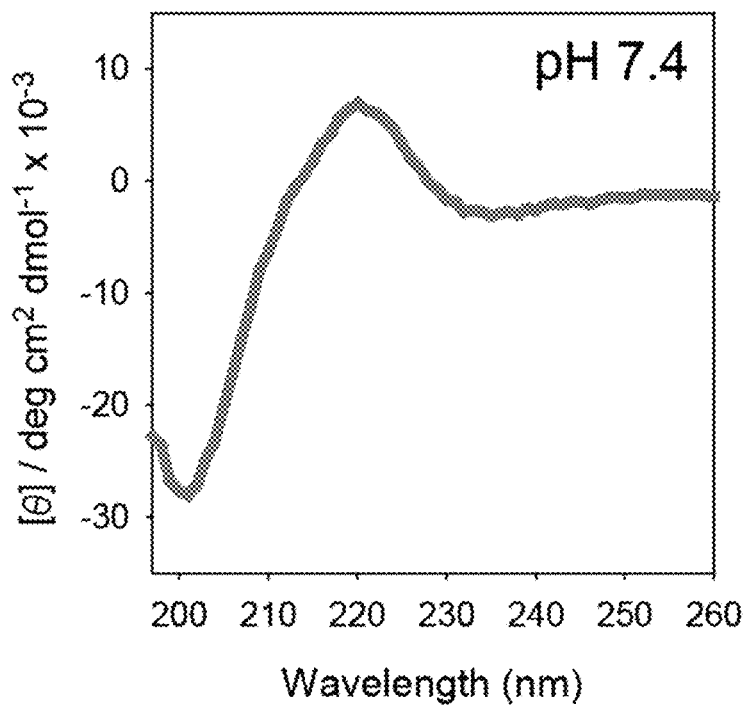
Figure 6:
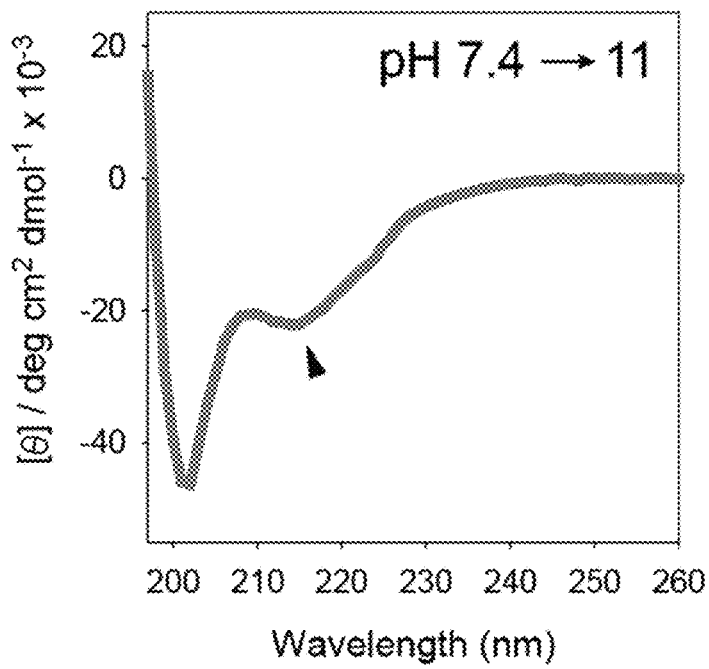
Figure 7:
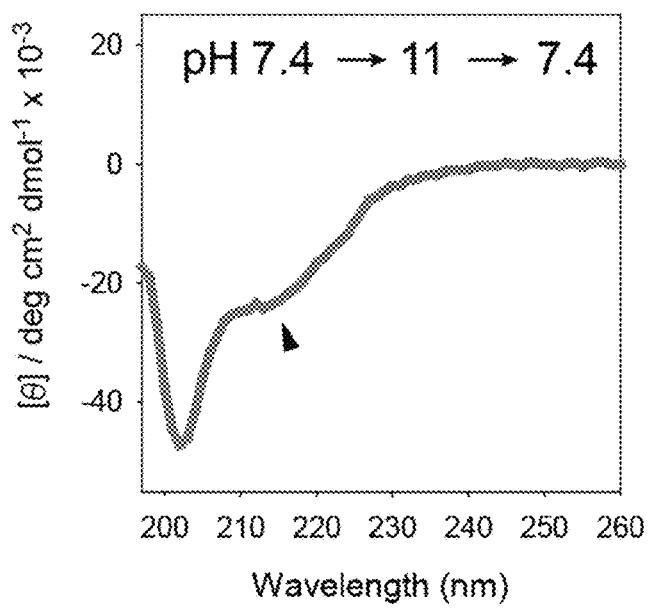
Figure 8:
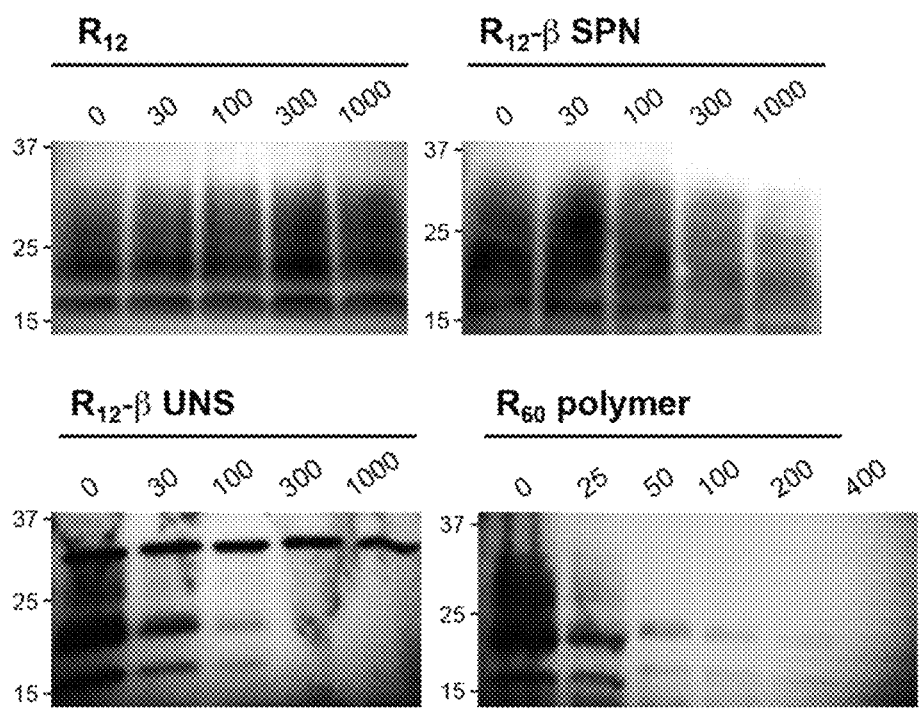
Figure 9:
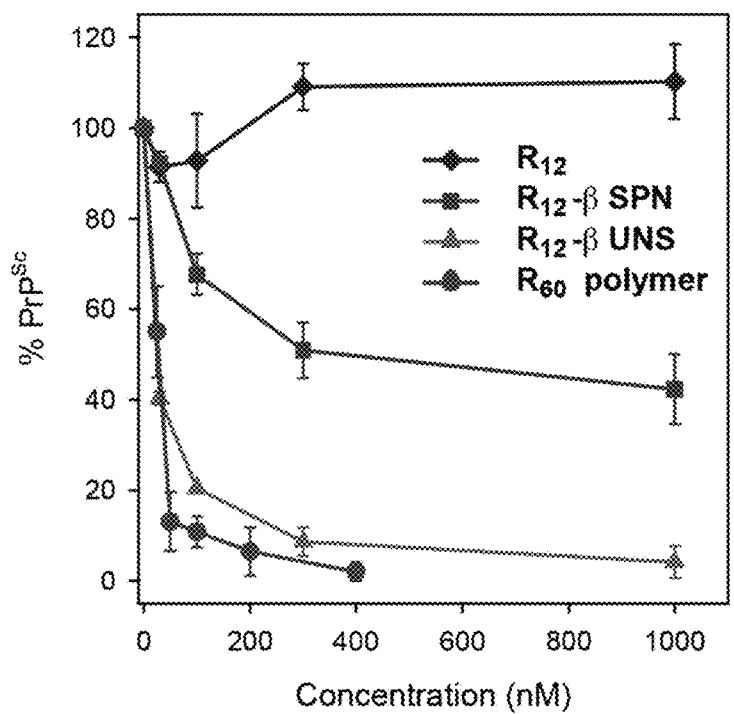
Figure 10:
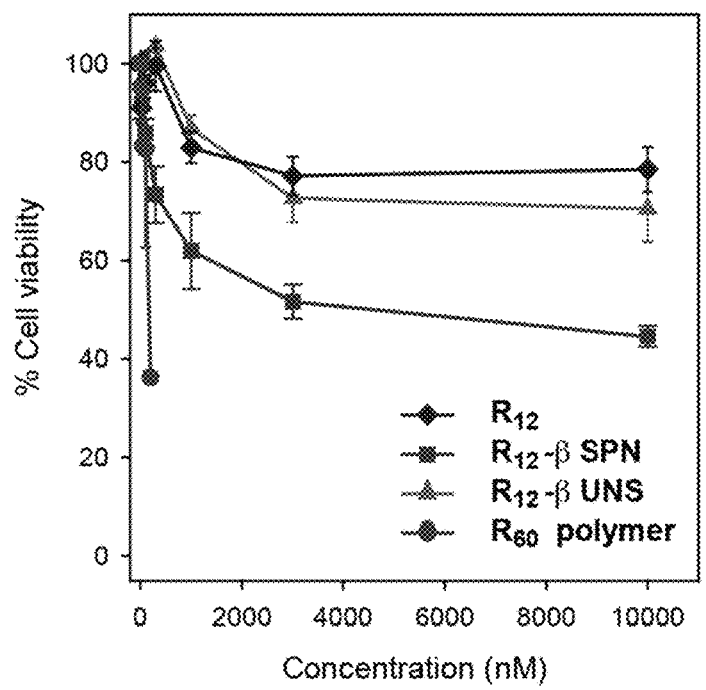

FIG. 5 shows the circular dichroism analysis of the fusion peptide of Example 3 in a phosphate buffer solution at pH 7.4 and 25° C. for identification of the secondary structure.

As seen from FIG. 5, it was confirmed that the fusion peptide of Example 3 could not be self-assembled to form a secondary structure.

This may be due to the strong electrostatic repulsion between the highly charged oligoarginine peptide ($R_{12}$) portions consisting of arginine residues. In self-assembly, the balance between attraction and repulsion is of great importance. It is thought that the electrostatic repulsion between the $R_{12}$ portions is stronger than the attraction between the β-sheet-forming segments due to β-sheet interaction.

Therefore, assuming that self-assembly will occur if the electrostatic repulsion is decreased by lowering the degree of protonation of arginine, self-assembly of the fusion peptide of Example 3 was attempted under a higher pH condition.

TEST EXAMPLE 3

Structural Analysis of Fusion Peptide Synthesized in Example 3 at pH 11

In order to investigate the secondary structure of the fusion peptide of Example 3 at pH 11, the pH of the solution containing the peptide was changed from 7.4 to 11 and then circular dichroism analysis was conducted. The result is shown in FIG. 6.

After the fusion peptide of Example 3 formed a nanostructure at pH 11, the pH was changed to 7.4 again and then circular dichroism analysis was conducted to confirm structural change. The result is shown in FIG. 7.

The fusion peptide of Example 3 was dissolved in 150 mM NaCl at first and the pH was adjusted using HCl and NaOH. The arrow on the graph indicates the minimum peak of the β-sheet (~216 nm).

FIG. 6 shows the circular dichroism analysis of the fusion peptide of Example 3 after the pH was changed from 7.4 to 11 and FIG. 7 shows the circular dichroism analysis of the fusion peptide of Example 3 after the pH was changed again to 7.4.

As seen from FIG. 6, it was confirmed that the peptide was self-assembled to a nanostructure via β-sheet interaction when the pH was increased to 11. After the nanostructure was formed, the structure was maintained stably even after the pH was changed again to 7.4.

TEST EXAMPLE 4

Measurement of Anti-prion Activity of Fusion Peptide of Example 3

Western blot was conducted as described above in order to confirm the change in the anti-prion activity of the fusion peptide of Example 3 due to structuring.

FIG. 8 shows the western blot result of the $PrP^{SC}$ having resistance to proteinase K in the ScN2a cells treated with the peptides of Example 3 ($R_{12}$-β), Comparative Example 2 ($R_{12}$) and Comparative Example 3 ($R_{60}$-polymer). FIG. 9 shows the relative $PrP^{SC}$ level determined by density measurement from the result of FIG. 8.

The peptide of Example 3, which was self-assembled to form a nanostructure when the pH was changed from 7.4 to pH 11 and stably maintained even after the pH was changed again to 7.4, was denoted as $R_{12}$-β SPN.

The peptide of Example 3 ($R_{12}$-β), which was not structured as the pH was fixed to 7.4, was denoted as $R_{12}$-β UNS.

It was expected that the $R_{12}$-β UNS, which was presumed to exist as single-molecular state, would exhibit the activity of a negative control group. However, as seen from FIG. 8 and FIG. 9, the $R_{12}$-β UNS, which did not form a nanostructure, exhibited 14.5 times higher anti-prion activity than the $R_{12}$-β SPN (fibrillar nanostructure similar to an amyloid). This anti-prion activity was comparable to that of the peptide Comparative Example 3 which contained 5 times more arginine residues.

In contrast, among the peptides of Example 3, the $R_{12}$-β SPN peptide, which formed a fibrillar nanostructure, exhibited anti-prion activity comparable to that of the peptide of Example 1 (Tat-β SPN).

TEST EXAMPLE 5

Measurement of Anti-prion Activity of Fusion Peptide of Example 3

FIG. 10 shows the cytotoxicity analysis of the peptides synthesized in Example 3 ($R_{12}$-β), Comparative Example 2 ($R_{12}$) and Comparative Example 3 ($R_{60}$-polymer) for ScN2a cells.

The fusion peptide of Example 3 was treated with the following three conditions to induce structural change and then anti-prion activity was measured.

1) $R_{12}$-β UNS: fusion peptide of Example 3 in single-molecule state which was unstructured by maintaining pH at 7.4.

2) $R_{12}$-β SPN (pH 7.4→11): fusion peptide of Example 3 formed into an amyloid-like fibrillar nanostructure through self-assembly by changing pH from 7.4 to 11 (pH 7.4→11).

3) $R_{12}$-β SPN ((pH 7.4→11→7.4): fusion peptide of Example 3 formed into an amyloid-like fibrillar nanostructure through self-assembly by changing pH from 7.4 to 11 and then again to 7.4 (pH 7.4→11→7.4).

The above two fusion peptides of Example 3 which formed amyloid-like fibrillar nanostructures were not differentiated specially unless necessary.

As seen from FIG. 10, the fusion peptide $R_{12}$-β UNS (Example 3, pH 7.4) which did not form a nanostructure, showed anti-prion activity comparable to that of the peptide of Comparative Example 3 but cytotoxicity was significantly different. Specifically, whereas the $R_{12}$-β UNS (Example 3, pH 7.4) exhibited low toxicity even at the high concentration of 10 μM, the peptide of Comparative Example 3 showed very how toxicity even at a very low concentration (0.2 μM).

The $R_{12}$-β SPN of Example 3 showed moderate cytotoxicity. The peptide of Comparative Example 1 consisting of 12 arginine residues exhibited remarkably low cytotoxicity, comparable to that of the $R_{12}$-β UNS of Example 3.

From the above result, it can be seen that the cell-penetrating peptide (CPP) contains a large number of arginine residues and, as the content of the polycationic arginine molecules increases, the number of cationic residues present in the peptide is increased and the cytotoxicity is also increased in proportion thereto. The cytotoxicity induced by the increased content of the arginine residues may be due to cell membrane perturbation.

However, the fusion peptide of Example 3 ($R_{12}$-β) exhibits low toxicity and superior anti-prion activity when it exists as the unstructured peptide ($R_{12}$-β UNS) at pH 7.4, even though it contains a large number of arginine residues.

To summarize, it was confirmed that, if the fusion peptide of Example 3 is maintained in the unstructured single-molecule state at pH 7.4, it exhibits remarkably low cytotoxicity while having anti-prion activity comparable to that of the peptide containing 5 times more arginine residues (R60-polymer). Specifically, the fusion peptide of Example 3 exhibits remarkably low cytotoxicity, with the cell survival rate maintained at 70% or higher at concentrations of 3000 nM of lower and above 60% even at high concentrations up to 10000 nM.

In addition, it was confirmed that the fusion peptide of Example 3 has remarkably higher anti-prion activity than the peptide consisting only of arginine residues of the same number ($R_{12}$). Specifically, it was confirmed that the fusion peptide of Example 3 exhibits remarkably superior anti-prion activity even at the very low concentration of 10 nM.

Meanwhile, it was confirmed that the fusion peptide of Example 3 experiences irreversible structural change to the amyloid-like fibrillar nanostructure under a basic condition. In this case, the cytotoxicity is increased to some extent and, at the same time, the anti-prion activity is decreased by 14.5 times or more as compared to the $R_{12}$-β UNS of Example 3.

Only because of the simple structural change depending on pH, the $R_{12}$-β UNS of Example 3 exhibits 14.5 times higher anti-prion activity and also difference in cytotoxicity as compared to the $R_{12}$-β SPN (amyloid-like fibrillar nanostructure) of Example 3.

The state of the $R_{12}$-β peptide depending on pH change was investigated in more detail.

TEST EXAMPLE 6

Analysis of Molecular State of Fusion Peptide of Example 3 Depending on pH Change It was confirmed from the above result that the fusion peptide of Example 3 experiences change into various molecular states depending on pH. In order to demonstrate this, nanostructure analysis was conducted in more detail by transmission electron microscopy (TEM) and atomic force microscopy (AFM).

Figure 11A:
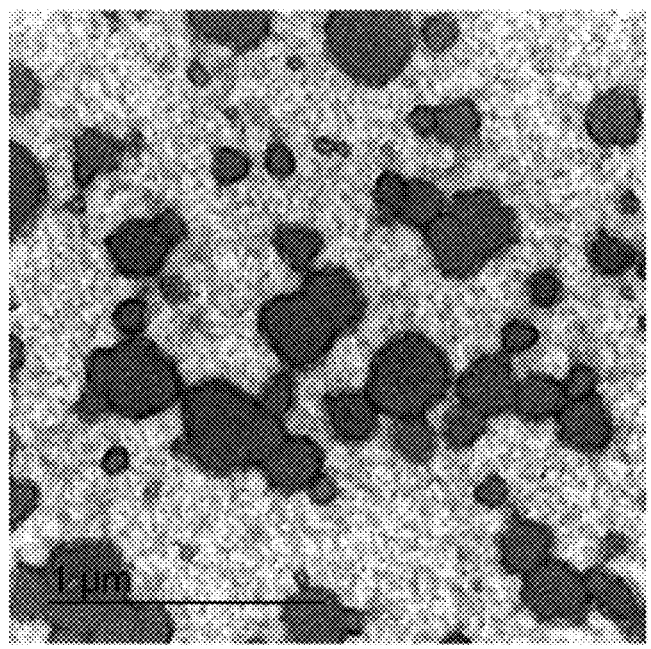
Figure 11B:
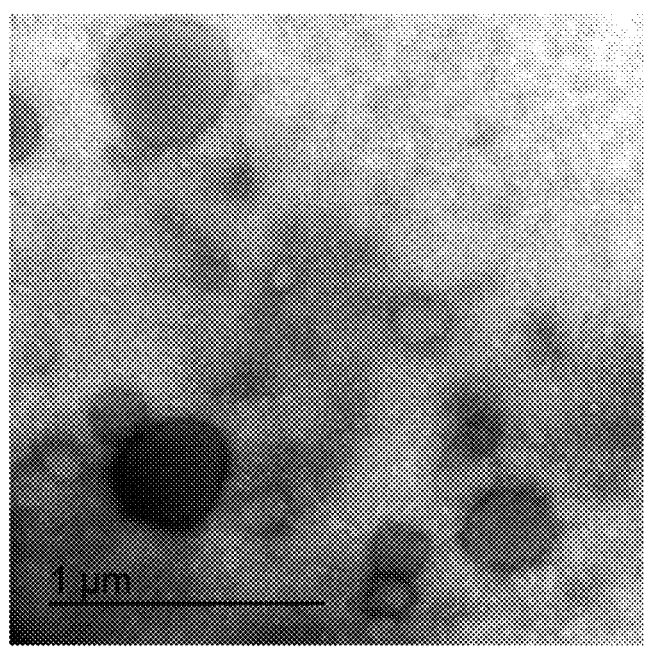
Figure 11C:
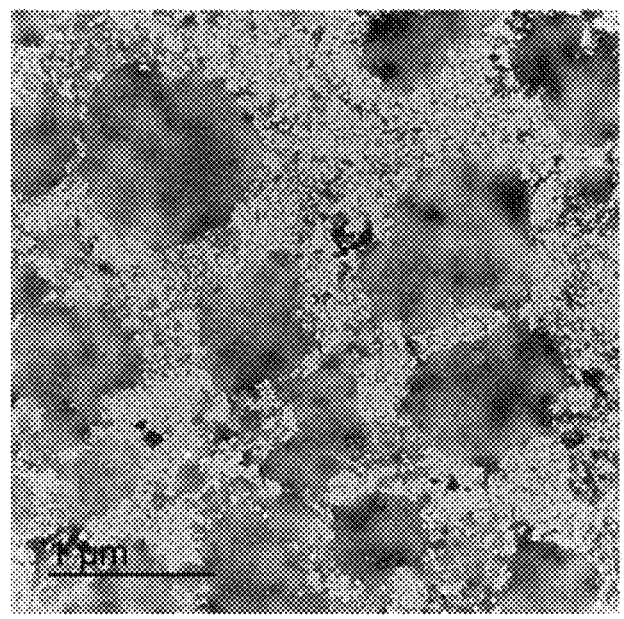
Figure 11D:
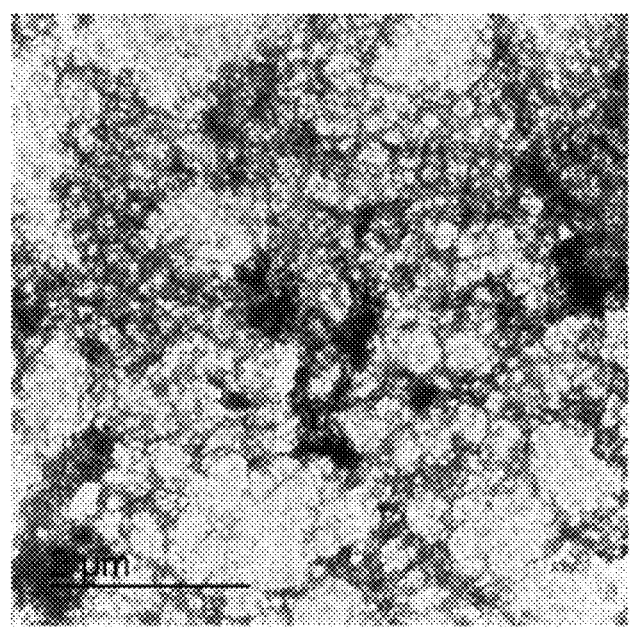

FIGS. 11A-11D show the negative-staining TEM images of the fusion peptide of Example 3, acquired to confirm the molecular state of the fusion peptide at a physiological salt concentration (150 mM NaCl) depending on pH change, at pH 3 (FIG. 11A), pH 5 (FIG. 11B), pH 7 (FIG. 11C) and pH 11 (FIG. 11D). The pH was adjusted using HCl or NaOH. The scale bar represents 1 μm.

Figure 12A:
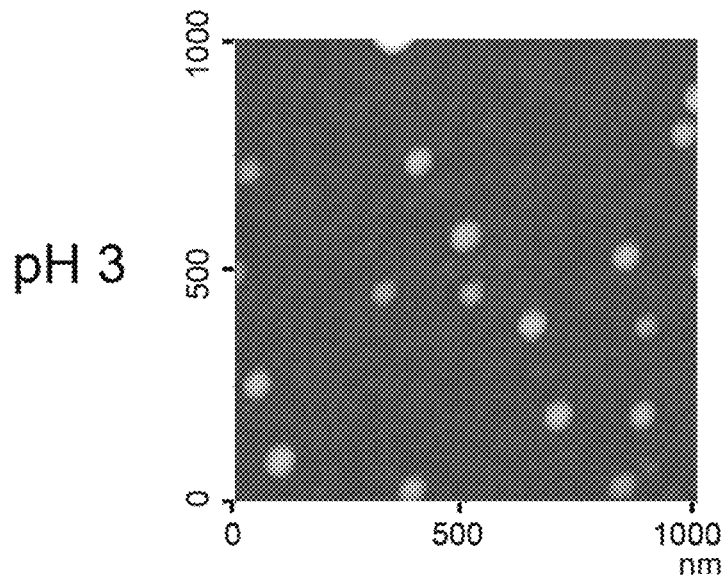
Figure 12B:
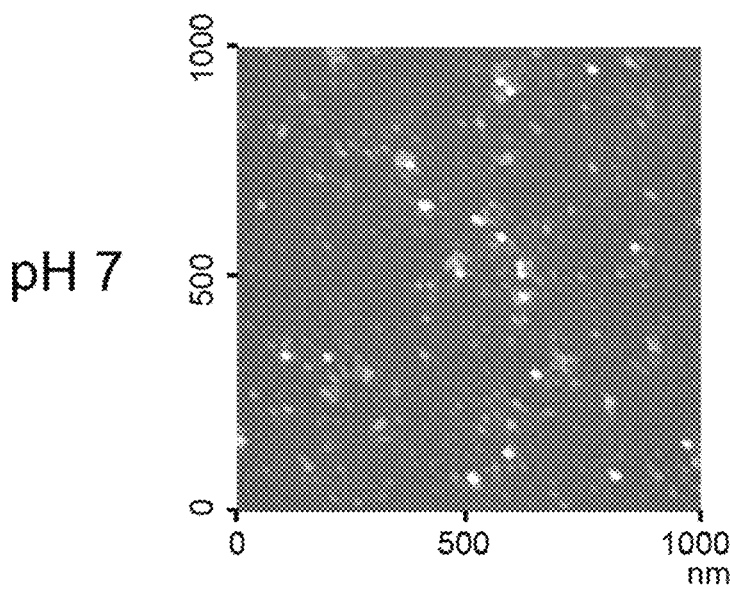
Figure 12C:
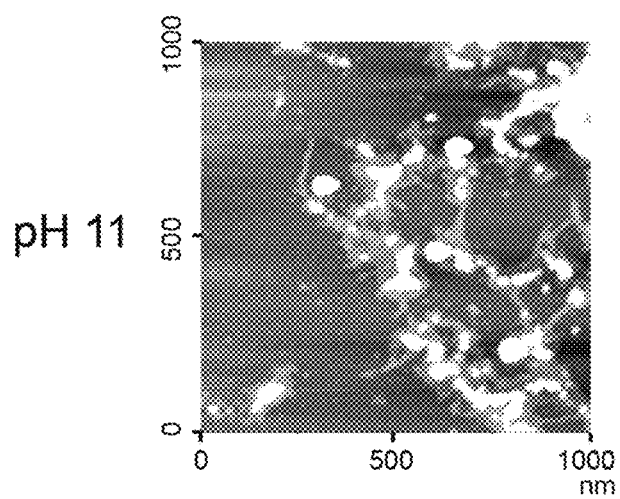

FIGS. 12A-12O show the AFM images of the fusion peptide of Example 3, acquired to confirm the molecular state of the fusion peptide at a physiological salt concentration (150 mM NaCl) depending on pH change, at pH 3 (FIG. 12A), pH 7 (FIG. 12B) and pH 11 (FIG. 12C).

Referring to FIGS. 11A-11D and FIGS. 12A-12C, it can be seen that the fusion peptide is self-assembled to form a vesicular nanostructure at pH 5 or lower.

At pH 7, the fusion peptide of Example 3 mainly existed as a small irregular aggregate and even a nanosheet was observed, which corresponds to an intermediate between the single-molecule state and the vesicular nanostructure.

At pH 11, the fusion peptide of Example 3 was self-assembled into a larger fibrillar aggregate, which was structurally similar to the amyloid aggregate.

To conclude the above results, it was confirmed that the fusion peptide of Example 3 experiences distinct structural and morphological change depending on solution pH and the anti-prion activity is also changed as a result thereof.

However, for cytotoxicity, the fusion peptide of Example 3 showed only insignificant change depending on solution pH and all the nanostructures exhibited significantly lower toxicity than the peptide of Comparative Example 3 consisting only of arginine residues.

Under the extracellular neutral condition, the fusion peptide of Example 3 hardly exhibited cytotoxicity even at high concentrations. Although the cytotoxicity was increased under the weakly acidic condition of the endosome and the lysosome in the cell, the increase was restricted only to the environment of the endosome and the lysosome in the cell. Because the fusion peptide of Example 3 is included in the endosome and the lysosome in the cell when administered into the cell, its cytotoxicity does not affect the survival of the cell.

If the fusion peptide of Example 3 which has been converted to the vesicular nanostructure under the weakly acidic condition is released out of the cell, its structure is changed to the structure with low cytotoxicity under the neutral condition. Accordingly, the fusion peptide does not exhibit cytotoxicity both inside and outside the cell.

TEST EXAMPLE 7

Analysis of Particle Size of Fusion Peptide of Example 3 at pH 3

Figure 13:
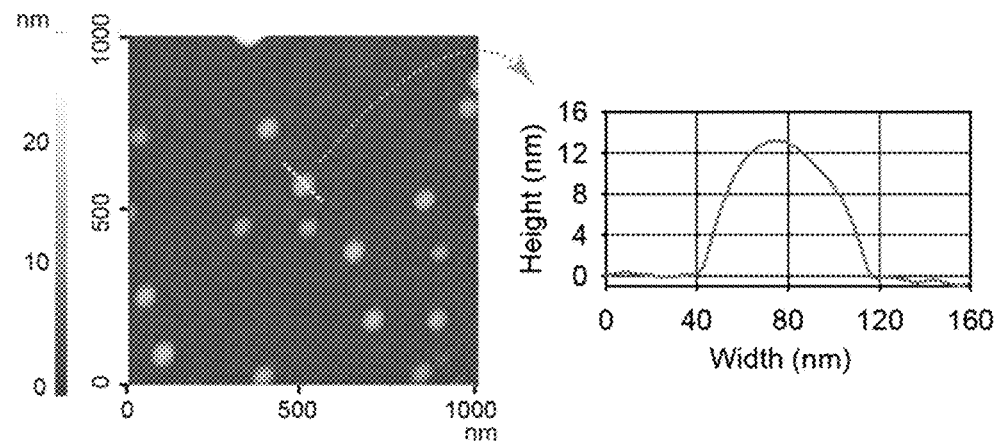

FIG. 13 shows the AFM image of the fusion peptide of Example 3 self-assembled into a vesicle at pH 3 and its height (nm) with respect to width (nm) measured therefrom.

From FIG. 13, it can be seen that the fusion peptide of Example 3 according to the present disclosure had a diameter of 20-90 nm when it was self-assembled to form a vesicular nanostructure at pH 3. More specifically, the vesicular nanostructure had an oval shape with a width of 50-100 nm on average, specifically 70-90 nm, and a height of 1-20 nm on average, specifically 8-16 nm.

TEST EXAMPLE 8

Figure 14:
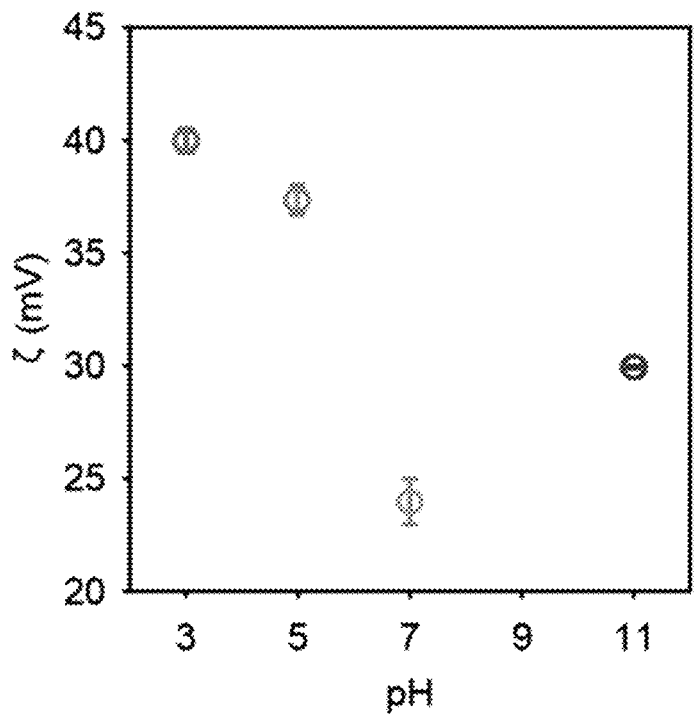

Analysis of Zeta Potential (ζ-potential) of Fusion Peptide of Example 3 Depending on pH FIG. 14 shows a result of measuring the zeta potential of the fusion peptide of Example 3 depending on pH. The pH was adjusted using HCl or NaOH and the data are represented as mean±standard deviation (n=3).

As seen from FIG. 14, the fusion peptide of Example 3 was self-assembled to form a vesicular nanostructure under the acidic condition (pH 3), which showed the highest zeta potential value. Specifically, the zeta potential was +40 mV at pH 3 and +38 mV at pH 5.

At pH 7, the fusion peptide of Example 3 was not self-assembled but remained in an unstructured and exhibited the lowest zeta potential. Specifically, the zeta potential was +24 mV at pH 7.

At pH 11, the fusion peptide of Example 3 was self-assembled to form a nanosheet-type nanostructure and had a moderate zeta potential value (+30 mV).

To conclude these results, it was confirmed that the morphology and surface charge of the nanostructure are changed depending on pH. Specifically, the fusion peptide of Example 3 has the highest positive charge when it forms a vesicular nanostructure under an acidic condition (pH 2-5.5) and its zeta potential is +14 to 18 mV higher as compared to the fusion peptide of Example 3 under a neutral condition, which has superior anti-prion activity.

Accordingly, it can be seen that the fusion peptide of Example 3 exhibits remarkably superior anti-prion activity when it forms a vesicular nanostructure under an acidic condition (pH 2-5.5) as compared to when it exists as an unstructured single-molecule form under a neutral condition (pH 6.0-9.0).

TEST EXAMPLE 9

Analysis of Zeta Potential (ζ-potential) of Fusion Peptide of Example 3 Depending on pH Change The change in zeta potential depending on the change of solution pH was investigated.

Figure 15:
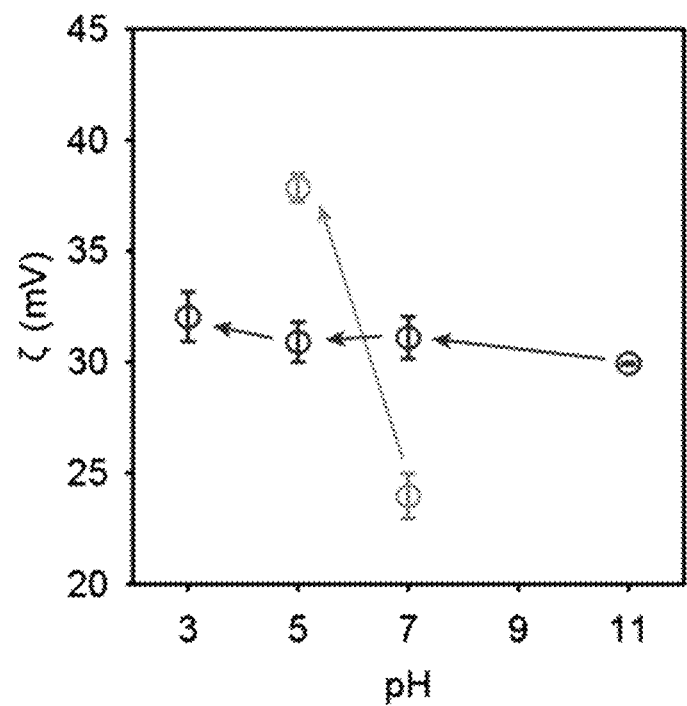

FIG. 15 shows a result of measuring the zeta potential of the fusion peptide of Example 3 when pH was changed from 7 to 5 (green) and when pH was changed sequentially from 11 to 7 to 5 and then to 3 (blue). The pH was adjusted using HCl or NaOH and the data are represented as mean±standard deviation (n=3).

As seen from FIG. 15, when the pH was changed from 7 to 5, the zeta potential was changed from +24 mV to +38 mV. In contrast, when the pH was changed sequentially from 11 to 7 to 5 and then to 3, the zeta potential was maintained constant with little change.

Figure 2A:
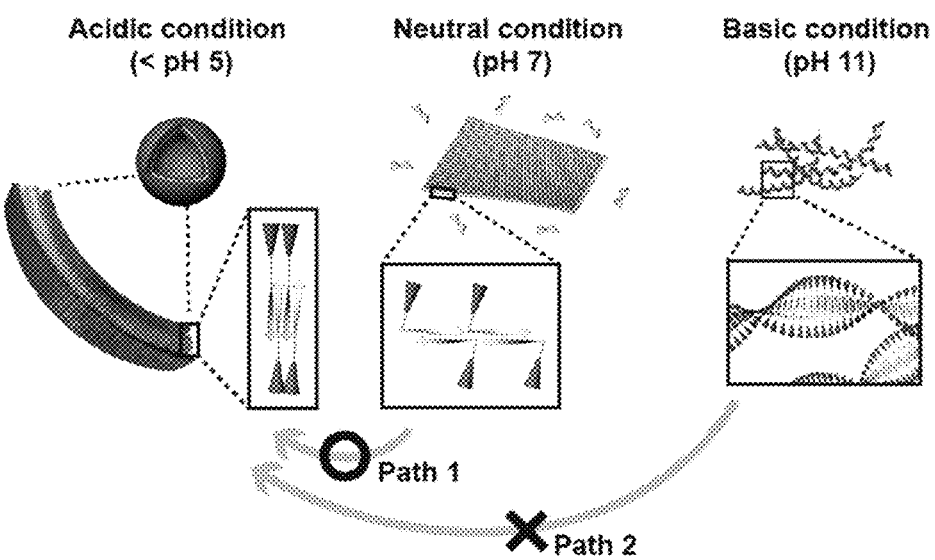
Figure 2B:
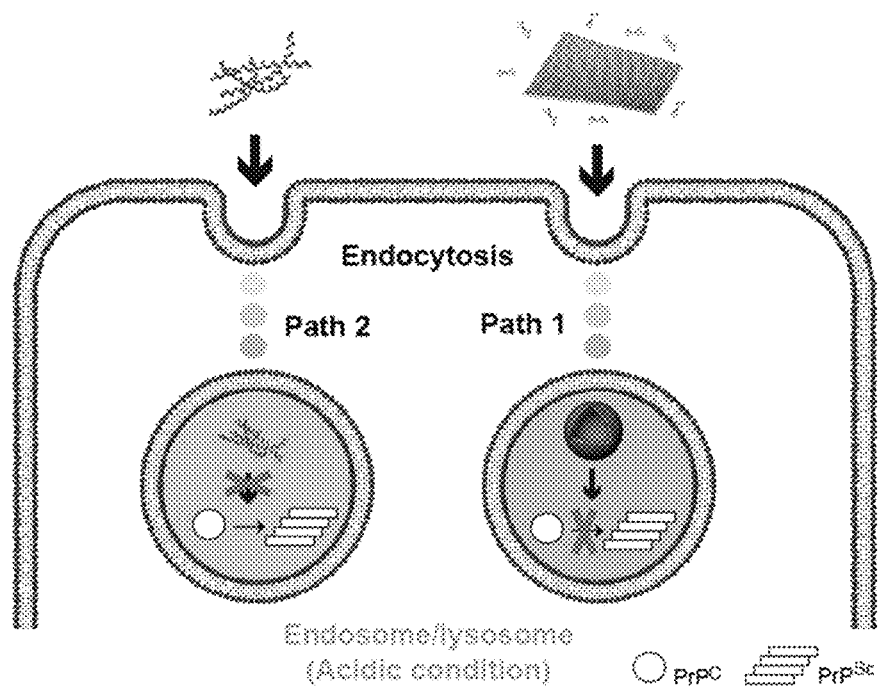

To conclude these experimental results, it can be seen that the fusion peptide according to the present disclosure, which contains the cell-penetrating peptide exhibiting a positive charge, having specifically 6-15 arginine residues, and the β-sheet-forming segment represented by Chemical Formula 1, exhibits the effect of inhibiting prion formation via the mechanism illustrated in FIGS. 2A and 2B.

TEST EXAMPLE 10

Figure 16:
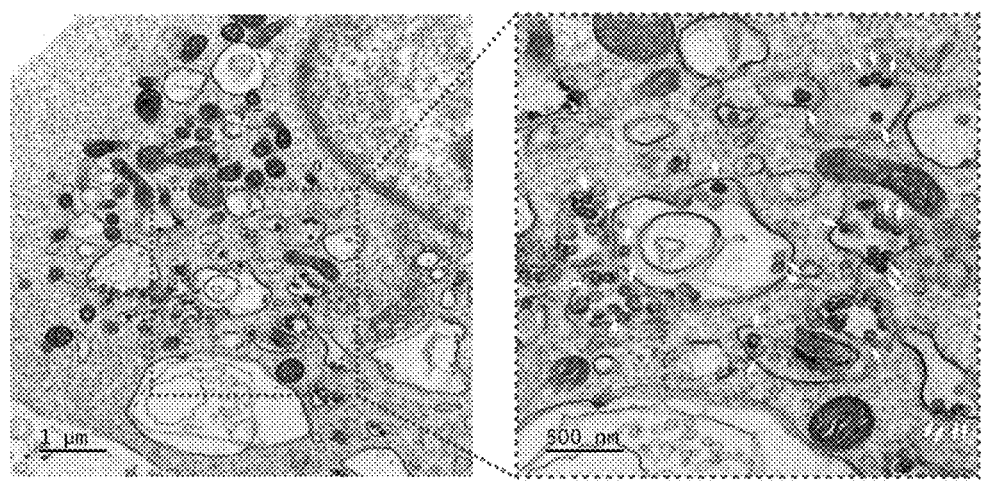

Analysis of Zeta Potential (ζ-potential) of Fusion Peptide of Example 3 Depending on pH Change FIG. 16 shows the transmission electron microscopic images of ScN2a cells treated with the $R_{12}$-β UNS of Example 3, which did not form a nanostructure, at pH 7. The arrows indicate $R_{12}$-β vesicles.

As seen from FIG. 16, it was confirmed that when the cells were treated with the $R_{12}$-β UNS of Example 3, which did not form a nanostructure, at pH 7, it was introduced into the vesicle such as the endosome or the lysosome of the cell via endocytosis and then self-assembled to a vesicular nanostructure under the low pH condition of the vesicle.

Because the vesicular nanostructure formed through self-assembly between fusion peptides exhibits higher anti-prion activity than the existing polymer consisting only of (about 60) arginine residues, it can prevent and inhibit the misfolding of only the proteins present in the vesicle.

TEST EXAMPLE 11

Structural Analysis of Fusion Peptides of Examples 4 and 5

Based on the above results, it was predicted that the fusion peptide of Example 4, which contains 13 or more arginine residues, would also change into various molecular states depending on pH. In order to demonstrate this, nanostructure analysis was conducted by atomic force microscopy (AFM).

Figure 19:
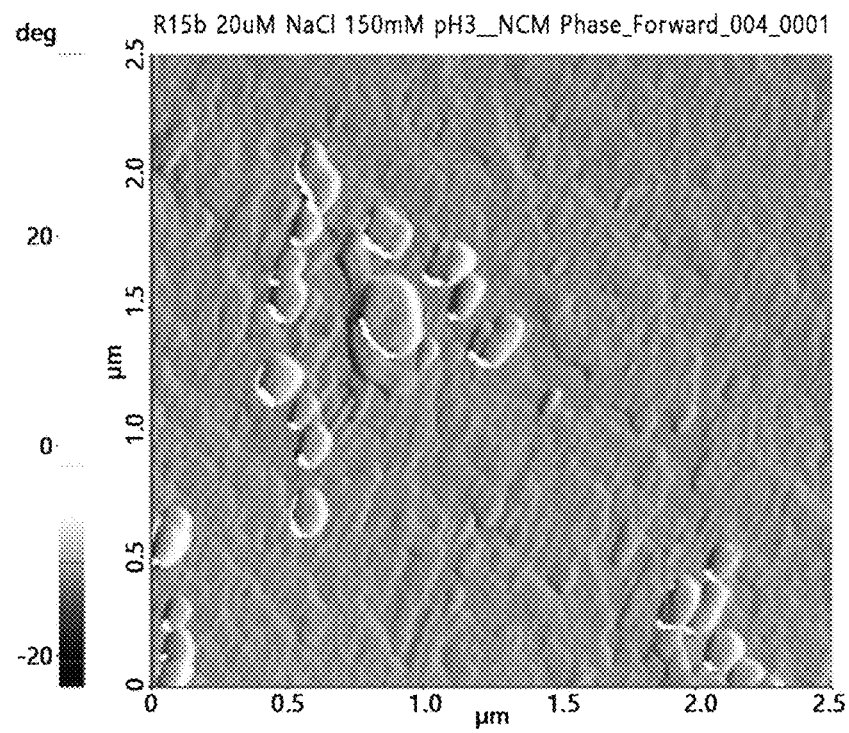
Figure 20:
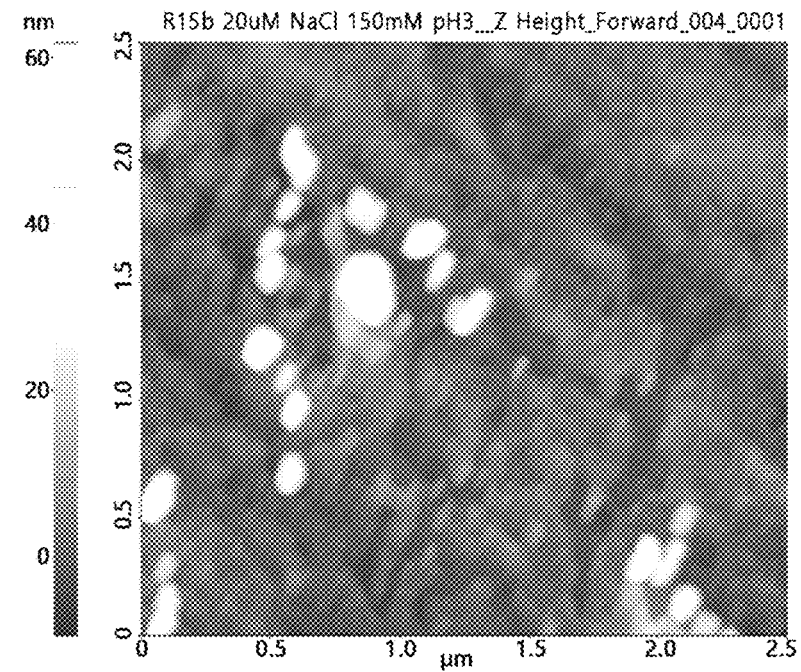

FIGS. 19 and 20 show the AFM images of the fusion peptide of Example 4 at pH 3 acquired to investigate whether the fusion peptide of Example 4 forms a vesicular nanostructure under physiological salt concentration (150 mM NaCl) and strongly acidic (pH 3) conditions. FIG. 19 is a phase image and FIG. 20 is a height image.

Referring to FIG. 19 and FIG. 20, it can be seen that the fusion peptide of Example 4 according to the present disclosure is also self-assembled under a strongly acidic condition (pH 3) to form a vesicular nanostructure reversibly.

That is to say, although the fusion peptide contains the cell-penetrating peptide exhibiting a positive charge, consisting of 14-15 arginine residues, it forms a vesicular nanostructure under an acidic condition (pH 2-5.5) through self-assembly between fusion peptides via hydrophobic interaction and electrostatic binding of the β-sheet-forming segment.

TEST EXAMPLE 12

Anti-prion Activity of Fusion Peptides of Examples 4 and 5

Western blot was conducted as described above in order to investigate the anti-prion activity of the fusion peptides of Examples 4 and 5 ($R_{14}$-β UNS, $R_{15}$-β UNS) that were not structured at pH 7.6.

Figure 21:
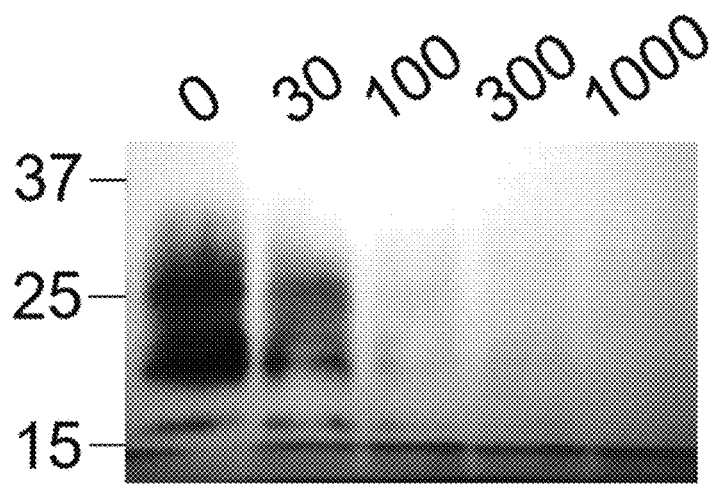
Figure 22:
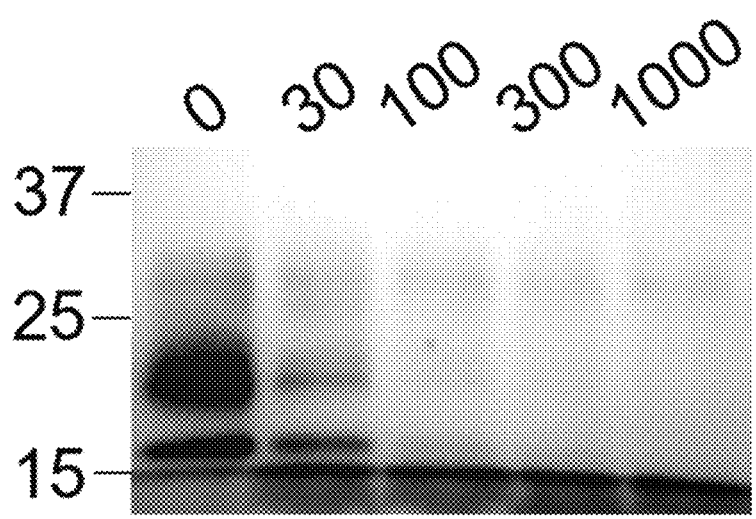

FIG. 21 shows the western blot result for the $PrP^{SC}$ having resistance to proteinase K in the ScN2a cells treated with the fusion peptide of Example 4 ($R_{14}$-β UNS). FIG. 22 shows the western blot result for the $PrP^{SC}$ having resistance to proteinase K in the ScN2a cells treated with the fusion peptide of Example 5 ($R_{15}$-β UNS) In FIGS. 21 and 22, the numbers below $R_{14}$-β UNS and $R_{15}$-β UNS indicate the concentration (nM) of the fusion peptide.

The anti-prion activity of the fusion peptides of Examples 4 and 5 in unstructured single-molecule states was measured by maintaining pH at 7.4.

As seen from FIGS. 21 and 22, both the fusion peptides of Examples 4 and 5 ($R_{14}$-β UNS, $R_{15}$-β UNS) showed remarkably high anti-prion activity even at the very low concentration of 30 nM.

To conclude this result with that of Test Example 11, it was confirmed that the fusion peptides of Examples 4 and 5 ($R_{14}$-β UNS, $R_{15}$-β UNS) have very high anti-prion activity in unstructured single-molecule states under neutral conditions (pH 6.0-9.0) and they form vesicular nanostructures with increased zeta potentials under acidic conditions (pH 2-5.5) as the fusion peptide of Example 3.

Accordingly, it can be seen that the fusion peptides of Examples 4 and 5 ($R_{14}$-β UNS, $R_{15}$-β UNS), like the fusion peptide of Example 3, exist in unstructured single-molecule states having low cytotoxicity and high anti-prion activity under neutral conditions (pH 6.0-9.0) and, upon uptake into the endosome and the lysosome of a cell via endocytosis, they reversibly form vesicular nanostructures having more increased anti-prion activity under acidic conditions (pH 2-5.5). Therefore, they can effectively inhibit abnormal protein aggregation or misfolding in the endosome and the lysosome.

What is claimed is:

1. A fusion peptide comprising the amino acid sequence selected from the group consisting of SEQ ID NOs:1, 3, 4, 13, and 14.

2. The fusion peptide according to claim 1, wherein the fusion peptide forms a nanostructure through self-assembly between fusion peptides via hydrophobic interaction and electrostatic binding of the β-sheet-forming segment under an acidic condition (pH 2-5.5).

3. The fusion peptide according to claim 2, wherein the nanostructure has a vesicular tertiary structure.

4. The fusion peptide according to claim 1, wherein the fusion peptide forms a nanostructure having an amyloid fibril-type tertiary structure through self-assembly between fusion peptides via hydrophobic interaction and electrostatic binding of the β-sheet-forming segment under a condition of pH 9.0-12 and the fibrillar nanostructure is stable regardless of pH change.

5. A pharmaceutical composition comprising the fusion peptide of claim 1, and a pharmaceutically acceptable carrier, excipient, or diluent.

6. The pharmaceutical composition according to claim 5, wherein the fusion peptide comprises the amino acid sequence of SEQ ID NO: 1.

7. The pharmaceutical composition according to claim 5, wherein the fusion peptide comprises the amino acid sequence of SEQ ID NO:3.

8. The pharmaceutical composition according to claim 5, wherein the fusion peptide comprises the amino acid sequence of SEQ ID NO:4.

9. The pharmaceutical composition according to claim 5, wherein the fusion peptide comprises the amino acid sequence of SEQ ID NO:13.

10. The pharmaceutical composition according to claim 5, wherein the fusion peptide comprises the amino acid sequence of SEQ ID NO:14.

* * * * *

SEQUENCE LISTING

<160> NUMBER OF SEQ ID NOS: 17

<210> SEQ ID NO 1
<211> LENGTH: 28
<212> TYPE: PRT

<213> ORGANISM: Artificial Sequence
<220> FEATURE:
<223> OTHER INFORMATION: pH-responsive fusion peptide R12-beta

<400> SEQUENCE: 1

Arg Arg Arg Arg Arg Arg Arg Arg Arg Arg Arg Arg Gly Ser Gly Gly
1               5                   10                  15

Phe Lys Phe Glu Phe Lys Phe Glu Phe Lys Phe Glu
            20                  25

<210> SEQ ID NO 2
<211> LENGTH: 32
<212> TYPE: PRT
<213> ORGANISM: Artificial Sequence
<220> FEATURE:
<223> OTHER INFORMATION: pH-responsive fusion peptide

<400> SEQUENCE: 2

Arg Arg Arg Arg Arg Arg Arg Arg Arg Arg Arg Arg Gly Ser Gly Gly
1               5                   10                  15

Phe Lys Phe Glu Phe Lys Phe Glu Phe Lys Phe Glu Phe Lys Phe Glu
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: pH-responsive fusion peptide R14-beta

<400> SEQUENCE: 3

Arg Arg Arg Arg Arg Arg Arg Arg Arg Arg Arg Arg Arg Arg Gly Ser
1               5                   10                  15

Gly Gly Phe Lys Phe Glu Phe Lys Phe Glu Phe Lys Phe Glu
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: pH-responsive fusion peptide R15-beta

<400> SEQUENCE: 4

Arg Arg Arg Arg Arg Arg Arg Arg Arg Arg Arg Arg Arg Arg Arg Gly
1               5                   10                  15

Ser Gly Gly Phe Lys Phe Glu Phe Lys Phe Glu Phe Lys Phe Glu
            20                  25                  30

<210> SEQ ID NO 5
<211> LENGTH: 36
<212> TYPE: PRT
<213> ORGANISM: Artificial Sequence
<220> FEATURE:
<223> OTHER INFORMATION: pH-responsive fusion peptide

<400> SEQUENCE: 5

Arg Arg Arg Arg Arg Arg Arg Arg Arg Arg Arg Arg Gly Ser Gly Gly
1               5                   10                  15

Phe Lys Phe Glu Phe Lys Phe Glu Phe Lys Phe Glu Phe Lys Phe Glu
            20                  25                  30

Phe Lys Phe Glu
        35

```
<210> SEQ ID NO 6
<211> LENGTH: 28
<212> TYPE: PRT
<213> ORGANISM: Artificial Sequence
<220> FEATURE:
<223> OTHER INFORMATION: pH-responsive fusion peptide

<400> SEQUENCE: 6

Arg Arg Arg Arg Arg Arg Arg Arg Arg Arg Arg Arg Gly Ser Gly Gly
 1               5                  10                  15

Trp Lys Trp Glu Trp Lys Trp Glu Trp Lys Trp Glu
                20                  25

<210> SEQ ID NO 7
<211> LENGTH: 32
<212> TYPE: PRT
<213> ORGANISM: Artificial Sequence
<220> FEATURE:
<223> OTHER INFORMATION: pH-responsive fusion peptide

<400> SEQUENCE: 7

Arg Arg Arg Arg Arg Arg Arg Arg Arg Arg Arg Arg Gly Ser Gly Gly
 1               5                  10                  15

Trp Lys Trp Glu Trp Lys Trp Glu Trp Lys Trp Glu Trp Lys Trp Glu
                20                  25                  30

<210> SEQ ID NO 8
<211> LENGTH: 36
<212> TYPE: PRT
<213> ORGANISM: Artificial Sequence
<220> FEATURE:
<223> OTHER INFORMATION: pH-responsive fusion peptide

<400> SEQUENCE: 8

Arg Arg Arg Arg Arg Arg Arg Arg Arg Arg Arg Arg Gly Ser Gly Gly
 1               5                  10                  15

Trp Lys Trp Glu Trp Lys Trp Glu Trp Lys Trp Glu Trp Lys Trp Glu
                20                  25                  30

Trp Lys Trp Glu
        35

<210> SEQ ID NO 9
<211> LENGTH: 28
<212> TYPE: PRT
<213> ORGANISM: Artificial Sequence
<220> FEATURE:
<223> OTHER INFORMATION: pH-responsive fusion peptide

<400> SEQUENCE: 9

Arg Arg Arg Arg Arg Arg Arg Arg Arg Arg Arg Arg Gly Ser Gly Gly
 1               5                  10                  15

Phe Lys Phe Asp Phe Lys Phe Asp Phe Lys Phe Asp
                20                  25

<210> SEQ ID NO 10
<211> LENGTH: 32
<212> TYPE: PRT
<213> ORGANISM: Artificial Sequence
<220> FEATURE:
<223> OTHER INFORMATION: pH-responsive fusion peptide

<400> SEQUENCE: 10

Arg Arg Arg Arg Arg Arg Arg Arg Arg Arg Arg Arg Gly Ser Gly Gly
 1               5                  10                  15
```

```
Phe Lys Phe Asp Phe Lys Phe Asp Phe Lys Phe Asp Phe Lys Phe Asp
            20                  25                  30
```

<210> SEQ ID NO 11
<211> LENGTH: 36
<212> TYPE: PRT
<213> ORGANISM: Artificial Sequence
<220> FEATURE:
<223> OTHER INFORMATION: pH-responsive fusion peptide

<400> SEQUENCE: 11

```
Arg Arg Arg Arg Arg Arg Arg Arg Arg Arg Arg Gly Ser Gly Gly
  1               5                  10                  15

Phe Lys Phe Asp Phe Lys Phe Asp Phe Lys Phe Asp Phe Lys Phe Asp
            20                  25                  30

Phe Lys Phe Asp
        35
```

<210> SEQ ID NO 12
<211> LENGTH: 32
<212> TYPE: PRT
<213> ORGANISM: Artificial Sequence
<220> FEATURE:
<223> OTHER INFORMATION: pH-responsive fusion peptide

<400> SEQUENCE: 12

```
Arg Arg Arg Arg Arg Arg Arg Arg Arg Arg Arg Gly Ser Gly Gly
  1               5                  10                  15

Trp Lys Trp Asp Trp Lys Trp Asp Trp Lys Trp Asp Trp Lys Trp Asp
            20                  25                  30
```

<210> SEQ ID NO 13
<211> LENGTH: 29
<212> TYPE: PRT
<213> ORGANISM: Artificial Sequence
<220> FEATURE:
<223> OTHER INFORMATION: fusion peptide Tat-beta

<400> SEQUENCE: 13

```
Gly Arg Lys Lys Arg Arg Gln Arg Arg Pro Pro Gln Gly Ser Gly
  1               5                  10                  15

Gly Phe Lys Phe Glu Phe Lys Phe Glu Phe Lys Phe Glu
            20                  25
```

<210> SEQ ID NO 14
<211> LENGTH: 14
<212> TYPE: PRT
<213> ORGANISM: Artificial Sequence
<220> FEATURE:
<223> OTHER INFORMATION: fusion peptide R2-beta

<400> SEQUENCE: 14

```
Arg Arg Phe Lys Phe Glu Phe Lys Phe Glu Phe Lys Phe Glu
  1               5                  10
```

<210> SEQ ID NO 15
<211> LENGTH: 13
<212> TYPE: PRT
<213> ORGANISM: Artificial Sequence
<220> FEATURE:
<223> OTHER INFORMATION: Tat

<400> SEQUENCE: 15

```
Gly Arg Lys Lys Arg Arg Gln Arg Arg Arg Pro Pro Gln
```

```
<210> SEQ ID NO 16
<211> LENGTH: 12
<212> TYPE: PRT
<213> ORGANISM: Artificial Sequence
<220> FEATURE:
<223> OTHER INFORMATION: R12

<400> SEQUENCE: 16

Arg Arg Arg Arg Arg Arg Arg Arg Arg Arg Arg Arg
 1               5                  10

<210> SEQ ID NO 17
<211> LENGTH: 60
<212> TYPE: PRT
<213> ORGANISM: Artificial Sequence
<220> FEATURE:
<223> OTHER INFORMATION: R60

<400> SEQUENCE: 17

Arg Arg Arg Arg Arg Arg Arg Arg Arg Arg Arg Arg Arg Arg Arg
 1               5                  10                  15

Arg Arg Arg Arg Arg Arg Arg Arg Arg Arg Arg Arg Arg Arg Arg
                20                  25                  30

Arg Arg Arg Arg Arg Arg Arg Arg Arg Arg Arg Arg Arg Arg Arg
                35                  40                  45

Arg Arg Arg Arg Arg Arg Arg Arg Arg Arg Arg Arg
                50                  55                  60
```